US007927811B2

(12) United States Patent
Sawada

(10) Patent No.: US 7,927,811 B2
(45) Date of Patent: Apr. 19, 2011

(54) POLYPEPTIDES HAVING BRAIN-LOCALIZING ACTIVITY AND USES THEREOF

(75) Inventor: Makoto Sawada, Aichi (JP)

(73) Assignee: Proteus Sciences Co., Ltd., Aichi (JP)

( * ) Notice: Subject to any disclaimer, the term of this patent is extended or adjusted under 35 U.S.C. 154(b) by 668 days.

(21) Appl. No.: 10/567,328

(22) PCT Filed: Aug. 6, 2004

(86) PCT No.: PCT/JP2004/011668
§ 371 (c)(1),
(2), (4) Date: Apr. 13, 2007

(87) PCT Pub. No.: WO2005/014625
PCT Pub. Date: Feb. 17, 2005

(65) Prior Publication Data
US 2008/0199436 A1    Aug. 21, 2008

(30) Foreign Application Priority Data

Aug. 8, 2003   (JP) ................................ 2003-289890

(51) Int. Cl.
| G01N 33/53 | (2006.01) |
|---|---|
| A61K 38/08 | (2006.01) |
| A61K 38/12 | (2006.01) |
| C07K 17/02 | (2006.01) |
| A61K 49/00 | (2006.01) |
| A61K 47/00 | (2006.01) |
| C12P 21/02 | (2006.01) |

(52) U.S. Cl. ......... 435/7.1; 530/300; 530/317; 530/333; 530/328; 514/1.2; 514/17.7; 424/9.1; 424/93.6; 424/417; 424/418; 424/450; 435/69.1

(58) Field of Classification Search ........................ None
See application file for complete search history.

(56) References Cited

U.S. PATENT DOCUMENTS

| 5,622,699 | A | * | 4/1997 | Ruoslahti et al. ................. 506/9 |
|---|---|---|---|---|
| 6,007,996 | A | | 12/1999 | McNamara et al. |
| 6,274,552 | B1 | | 8/2001 | Tamarkin et al. |
| 6,562,958 | B1 | * | 5/2003 | Breton et al. ................. 536/23.7 |
| 7,214,786 | B2 | * | 5/2007 | Kovalic et al. ................. 536/23.6 |
| 2007/0254316 | A1 | * | 11/2007 | Rodriguez et al. .......... 435/7.23 |
| 2007/0269523 | A1 | | 11/2007 | Sawada et al. |
| 2009/0092583 | A1 | | 4/2009 | Sawada et al. |
| 2010/0111838 | A1 | | 5/2010 | Nakajo et al. |

FOREIGN PATENT DOCUMENTS

| JP | 8-511236 T | 11/1996 |
|---|---|---|
| JP | 11-92406 A | 4/1999 |
| JP | 2004-073964 A | 3/2004 |
| WO | WO 02/087509 A2 | 11/2002 |
| WO | WO 03/009881 A2 | 2/2003 |
| WO | WO 03/020751 A2 | 3/2003 |
| WO | WO 2004/015392 A2 | 2/2004 |

OTHER PUBLICATIONS

Muruganandam et al., "Selection of phage-displayed llama single-domain antibodies that transmigrate across human blood-brain barrier endothelium," FASEB J., Feb. 2002, vol. 16, No. 2, pp. 240-242.
Shi et al., "Noninvasive gene targeting to the brain," Proc. Natl. Acad. Sci. USA, Jun. 2000, vol. 97, No. 13, pp. 7567-7572.
Imai et al., "Migration activity of microglia and macrophages into rat brain," Neuroscience Letters, 1997, 237:49-52.
Kang et al., "Stability of the Disulfide Bond in an Avidin-Biotin Linked Chimeric Peptide During in vivo Transcytosis Through Brain Endothelial Cells", Journal of Drug Targeting, 2000, vol. 8, No. 6, pp. 425-434.
Pasqualini et al., "Organ targeting in vivo using phage display in vivo using phage display peptide libraries", Nature, 1996, vol. 380, No. 6572, pp. 364-366.
Sawada et al., "Brain-specific gene expression by immortalized microglial cell-mediated gene transfer in the mammalian brain", FEBS Letters, 1998, vol. 433, pp. 37-40.
Schwarze, et al., "In vivo protein transduction: delivery of a biologically active protein into the mouse", Science, 1999, vol. 285, No. 5433, pp. 1569-1572.
R. Pasqualini et al., "Organ targeting in vivo using phage display in vivo using phage display peptide libraries", Nature, 1996, vol. 380, No. 6572, pp. 364-366.
S.R. Schwarze, et al., "In vivo protein transduction: delivery of a biologically active protein into the mouse", Science, 1999, vol. 285, No. 5433, pp. 1569-1572.
Young-Sook Kang et al., "Stability of the Disulfide Bond in an Avidin-Biotin Linked Chimeric Peptide During in vivo Transcytosis Through Brain Endothelial Cells", Journal of Drug Targeting, 2000, vol. 8, No. 6, pp. 425-434.
Makoto Sawada et al., "Brain-specific gene expression by immortalized microglial cell-mediated gene transfer in the mammalian brain", FEBS Letters, 1998, vol. 433, pp. 37-40.
Egleton et al., "Transport of Opioid Peptides into the Central Nervous System," Journal of Pharmaceutical Sciences, Nov. 1998, 87(11):1433-1439.

(Continued)

*Primary Examiner* — Elizabeth C. Kemmerer
*Assistant Examiner* — Kimberly A. Ballard
(74) *Attorney, Agent, or Firm* — Foley & Lardner LLP

(57) ABSTRACT

The present invention relates to polypeptides having a brain-localizing activity, molecules comprising these polypeptides, and pharmaceutical agents that confer brain-localizing activity. The present inventors are the first to reveal amino acid motif sequences involved in brain-localizing activity. Polypeptides that comprise such motif sequences and have brain localizing activity were discovered as follows: DNAs encoding polypeptides comprising random amino acid sequences were synthesized, and incorporated into a phage library. The phage library produced was used to screen for polypeptides having brain-localized activity, which yielded such several polypeptides. These polypeptides comprised common sequences, which lead to the successful discovery of amino acid motif sequences involved in brain-localizing activity. The polypeptides of the present invention comprising the motif sequences specifically bind to cerebrovascular endothelial cells, and induce a transcellular pathway that enables brain-specific targeting and transport of substances in the cerebral parenchyma, which was not possible prior to the present invention.

14 Claims, 24 Drawing Sheets

OTHER PUBLICATIONS

Piwko et al., "Localization and Pharmacological Characterization of Somatostatin Recognition Sites in the Human Cerebellum," Neuropharmacology, Jun. 1996, 35(6):713-723.

Supplementary European Search Report mailed Apr. 8, 2009, in European Patent Application EP 06783020), 4 pages.

Boder et al., "Yeast surface display for screening combinatorial polypeptide libraries," Nature Biotechnology, Jun. 1, 1997, 15:553-557.

Kim et al., "Human neural stem cells genetically modified for brain repair in neurological disorders," Neuropathology: Official Journal of the Japanese Society of Neuropathology, Sep. 2004, 24(3):159-171.

Kondo et al., "Yeast cell-surface display-applications of molecular display," Applied Microbiology and Biotechnology, Mar. 1, 2004, 64(1):28-40.

Laakkonen et al., "A tumor-homing peptide with a targeting specificity related to lymphatic vessels," Nature Medicine, Jun. 10, 2002, 8(7):751-755.

Laakkonen et al., "Antitumor activity of a homing peptide that targets tumor lymphatics and tumor cells," Proc. Natl. Acad. Sci., Jun. 22, 2004, 101(25):9381-9386.

Makar et al., "Brain-derived neurotrophic factor (BDNF) gene delivery into the CNS using bone marrow cells as vehicles in mice," Neuroscience Letters, Feb. 17, 2004, 356:215-219.

Bickel et al., "In Vivo Demonstration of Subcellular Localization of Anti-transferrin Receptor Monoclonal Antibody-Colloidal Gold Conjugate in Brain Capillary Endothelium," The Journal of Histochemistry and Cytochemistry, 1994, 42(11):1493-1497.

* cited by examiner

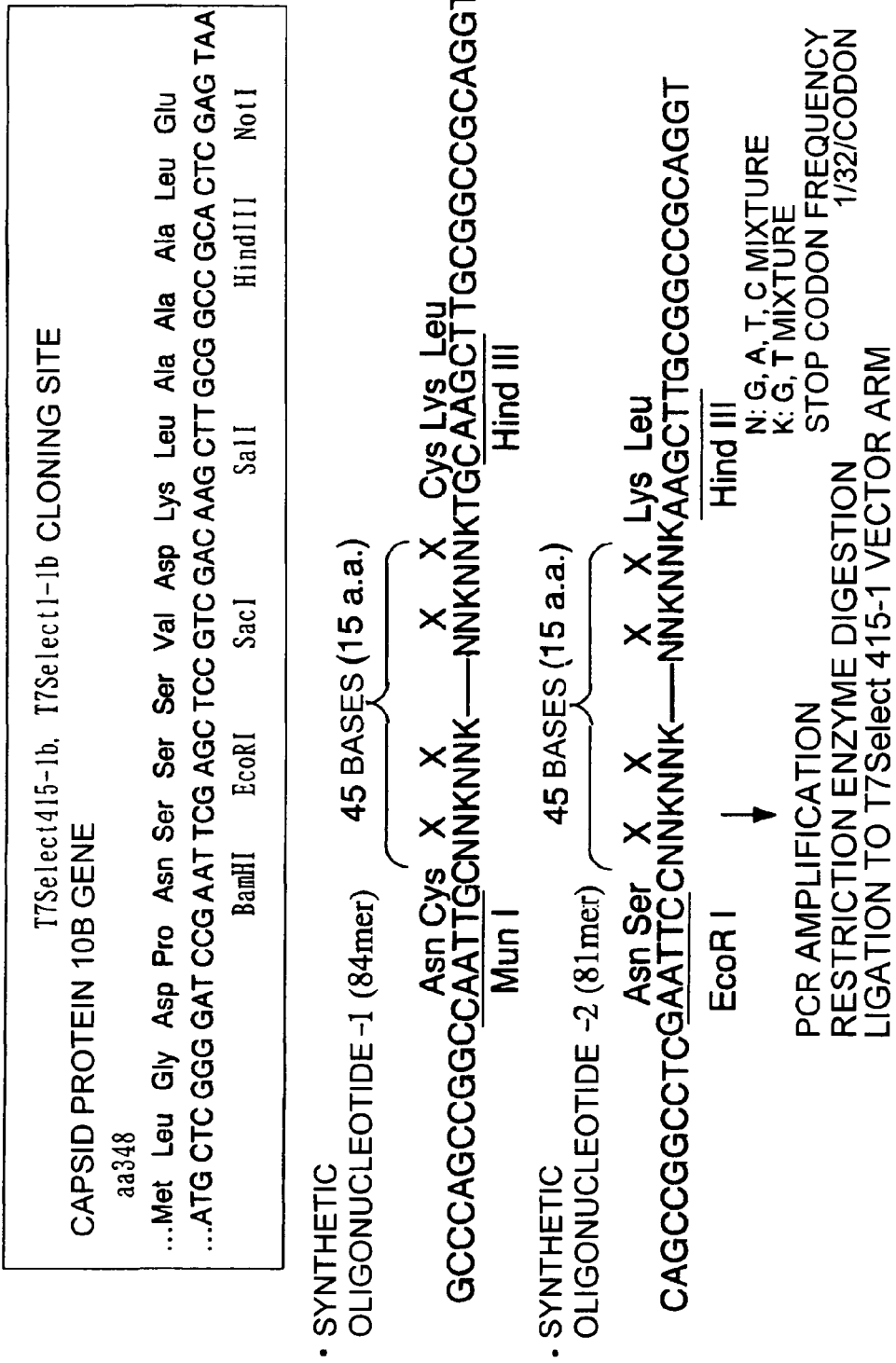

FIG. 4

T7 Select SYSTEM

- T7Select415-1
  - IN WILD TYPE, PARTS OF THE CAPSID ARE PRODUCED FROM 10A AND 10B BY FRAMESHIFT. HEREIN, THE CAPSID IS MADE OF ONLY 10B.
  - 415 PEPTIDES CAN BE DISPLAYED ON THE EXTERIOR OF THE CAPSID AS LONG AS THEY ARE UNDER 50 aa.

- 415-c15c LIBRARY
  - Cys-FLANKED 15-aa RANDOM PEPTIDES WERE INSERTED.
  - TGCNNKNNKNNKNNKNNKNNKNNKNNK NNKNNKNNKNNKNNKNNKNNKTGC
  - K=G or T, N=A, C, G or T
  - VARIANT = ABOUT $10^7$

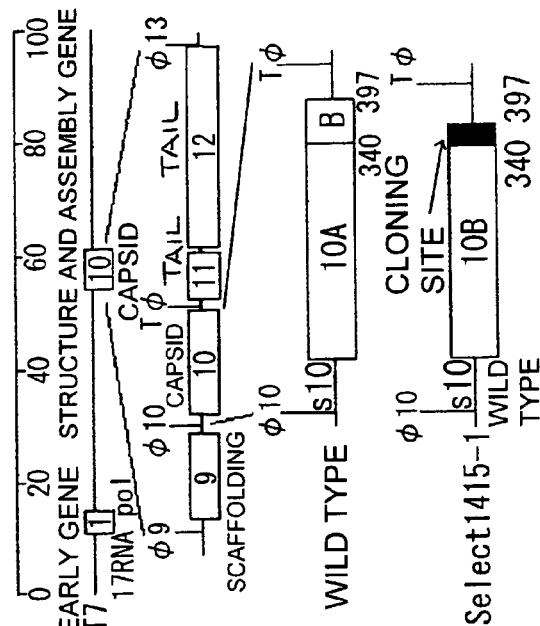

PANNING METHOD

- SELECTION METHOD UTILIZING PROTEIN INTERACTION
  - SELECTIVE CONCENTRATION OF CELL SURFACE-ADSORBED PHAGES
  - IMPORTANT PARAMETERS
    - CARRIER SELECTION
    - ADSORPTION CONDITIONS
    - REMOVAL OF NON-SPECIFICALLY-BOUND PHAGES
    - PHAGE VS CELL
    - PHAGE VS PROTEIN OR LYSATE

BIOTIN

GREEN:ZO-1 / RED:MICROGLIA / BLUE:NUCLEUS

FIG. 19
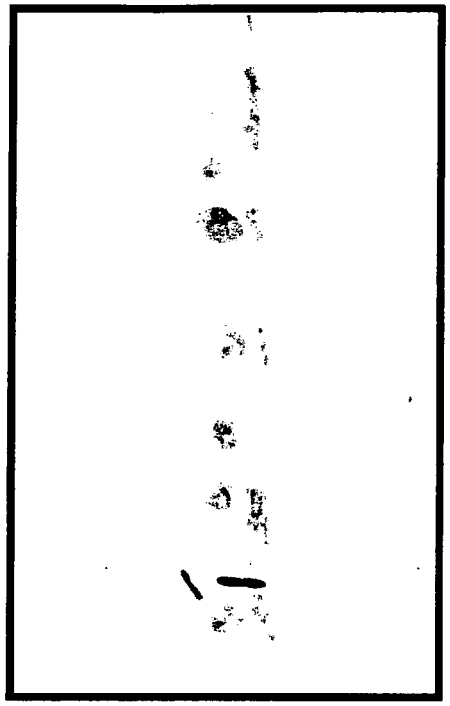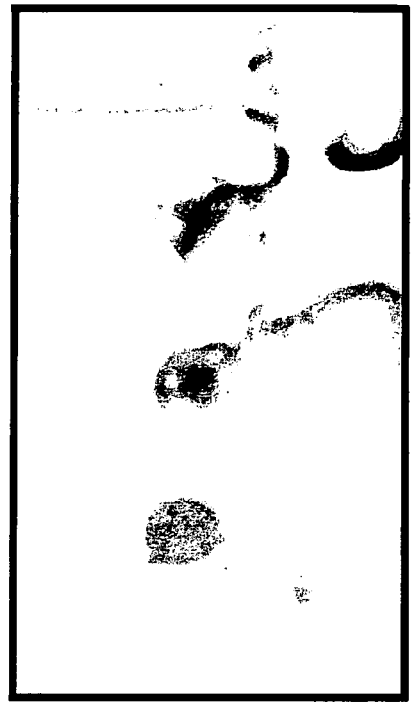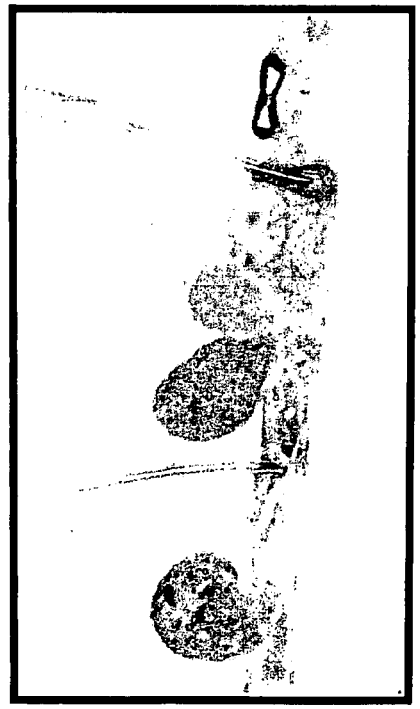

0.2 μm and USES THEREOF

SEQUENCE LISTING

```
<160> NUMBER OF SEQ ID NOS: 24

<210> SEQ ID NO 1
<211> LENGTH: 9
<212> TYPE: PRT
<213> ORGANISM: Artificial
<220> FEATURE:
<223> OTHER INFORMATION: an artificially synthesized sequence

<400> SEQUENCE: 1

Cys Ser Asn Leu Leu Ser Arg His Cys
1               5

<210> SEQ ID NO 2
<211> LENGTH: 9
<212> TYPE: PRT
<213> ORGANISM: Artificial
<220> FEATURE:
<223> OTHER INFORMATION: an artificially synthesized sequence

<400> SEQUENCE: 2

Cys Ser Leu Asn Thr Arg Ser Gln Cys
1               5

<210> SEQ ID NO 3
```

```
<211> LENGTH: 9
<212> TYPE: PRT
<213> ORGANISM: Artificial
<220> FEATURE:
<223> OTHER INFORMATION: an artificially synthesized sequence

<400> SEQUENCE: 3

Cys Val Ala Pro Ser Arg Ala Thr Cys
1               5

<210> SEQ ID NO 4
<211> LENGTH: 9
<212> TYPE: PRT
<213> ORGANISM: Artificial
<220> FEATURE:
<223> OTHER INFORMATION: an artificially synthesized sequence

<400> SEQUENCE: 4

Cys Val Val Arg His Leu Gln Gln Cys
1               5

<210> SEQ ID NO 5
<211> LENGTH: 9
<212> TYPE: PRT
<213> ORGANISM: Artificial
<220> FEATURE:
<223> OTHER INFORMATION: an artificially synthesized sequence

<400> SEQUENCE: 5

Cys Val Leu Arg His Leu Gln Gln Cys
1               5

<210> SEQ ID NO 6
<211> LENGTH: 9
<212> TYPE: PRT
<213> ORGANISM: Artificial
<220> FEATURE:
<223> OTHER INFORMATION: an artificially synthesized sequence

<400> SEQUENCE: 6

Cys Arg Gln Leu Val Gln Val His Cys
1               5

<210> SEQ ID NO 7
<211> LENGTH: 9
<212> TYPE: PRT
<213> ORGANISM: Artificial
<220> FEATURE:
<223> OTHER INFORMATION: an artificially synthesized sequence

<400> SEQUENCE: 7

Cys Gly Pro Leu Lys Thr Ser Ala Cys
1               5

<210> SEQ ID NO 8
<211> LENGTH: 9
<212> TYPE: PRT
<213> ORGANISM: Artificial
<220> FEATURE:
<223> OTHER INFORMATION: an artificially synthesized sequence

<400> SEQUENCE: 8

Cys Leu Lys Pro Gly Pro Lys His Cys
1               5

<210> SEQ ID NO 9
<211> LENGTH: 9
<212> TYPE: PRT
```

```
<213> ORGANISM: Artificial
<220> FEATURE:
<223> OTHER INFORMATION: an artificially synthesized sequence

<400> SEQUENCE: 9

Cys Arg Ser Pro Gln Pro Ala Val Cys
1               5

<210> SEQ ID NO 10
<211> LENGTH: 9
<212> TYPE: PRT
<213> ORGANISM: Artificial
<220> FEATURE:
<223> OTHER INFORMATION: an artificially synthesized sequence

<400> SEQUENCE: 10

Cys Asn Pro Leu Ser Pro Arg Ser Cys
1               5

<210> SEQ ID NO 11
<211> LENGTH: 9
<212> TYPE: PRT
<213> ORGANISM: Artificial
<220> FEATURE:
<223> OTHER INFORMATION: an artificially synthesized sequence

<400> SEQUENCE: 11

Cys Pro Ala Gly Ala Val Lys Ser Cys
1               5

<210> SEQ ID NO 12
<211> LENGTH: 9
<212> TYPE: PRT
<213> ORGANISM: Artificial
<220> FEATURE:
<223> OTHER INFORMATION: an artificially synthesized sequence

<400> SEQUENCE: 12

Cys Pro Ala Gly Ala Leu Lys Ser Cys
1               5

<210> SEQ ID NO 13
<211> LENGTH: 16
<212> TYPE: DNA
<213> ORGANISM: Artificial
<220> FEATURE:
<223> OTHER INFORMATION: an artificially synthesized primer sequence

<400> SEQUENCE: 13
gtatgggata aacaac                                                      16

<210> SEQ ID NO 14
<211> LENGTH: 81
<212> TYPE: DNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (19)..(20)
<223> OTHER INFORMATION: "n" = a, t, g, or c.
<220> FEATURE:
<221> NAME/KEY: misc_feature
<222> LOCATION: (22)..(23)
<223> OTHER INFORMATION: "n" = a, t, g, or c.
<220> FEATURE:
<221> NAME/KEY: misc_feature
<222> LOCATION: (25)..(26)
<223> OTHER INFORMATION: "n" = a, t, g, or c.
<220> FEATURE:
```

```
<221> NAME/KEY: misc_feature
<222> LOCATION: (28)..(29)
<223> OTHER INFORMATION: "n" = a, t, g, or c.
<220> FEATURE:
<221> NAME/KEY: misc_feature
<222> LOCATION: (31)..(32)
<223> OTHER INFORMATION: "n" = a, t, g, or c.
<220> FEATURE:
<221> NAME/KEY: misc_feature
<222> LOCATION: (34)..(35)
<223> OTHER INFORMATION: "n" = a, t, g, or c.
<220> FEATURE:
<221> NAME/KEY: misc_feature
<222> LOCATION: (37)..(38)
<223> OTHER INFORMATION: "n" = a, t, g, or c.
<220> FEATURE:
<221> NAME/KEY: misc_feature
<222> LOCATION: (40)..(41)
<223> OTHER INFORMATION: "n" = a, t, g, or c.
<220> FEATURE:
<221> NAME/KEY: misc_feature
<222> LOCATION: (43)..(44)
<223> OTHER INFORMATION: "n" = a, t, g, or c.
<220> FEATURE:
<221> NAME/KEY: misc_feature
<222> LOCATION: (46)..(47)
<223> OTHER INFORMATION: "n" = a, t, g, or c.
<220> FEATURE:
<221> NAME/KEY: misc_feature
<222> LOCATION: (49)..(50)
<223> OTHER INFORMATION: "n" = a, t, g, or c.
<220> FEATURE:
<221> NAME/KEY: misc_feature
<222> LOCATION: (52)..(53)
<223> OTHER INFORMATION: "n" = a, t, g, or c.
<220> FEATURE:
<221> NAME/KEY: misc_feature
<222> LOCATION: (55)..(56)
<223> OTHER INFORMATION: "n" = a, t, g, or c.
<220> FEATURE:
<221> NAME/KEY: misc_feature
<222> LOCATION: (58)..(59)
<223> OTHER INFORMATION: "n" = a, t, g, or c.
<220> FEATURE:
<221> NAME/KEY: misc_feature
<222> LOCATION: (61)..(62)
<223> OTHER INFORMATION: "n" = a, t, g, or c.

<400> SEQUENCE: 14
gaatccatgc agaatttcnn knnknnknnk nnknnknnkn nknnknnknn knnknnknnk      60
nnkaagcctg ctacagacca t                                               81

<210> SEQ ID NO 15
<211> LENGTH: 86
<212> TYPE: DNA
<213> ORGANISM: Artificial
<220> FEATURE:
<223> OTHER INFORMATION: an artificially synthesized sequence
<220> FEATURE:
<221> NAME/KEY: misc_feature
<222> LOCATION: (21)..(22)
<223> OTHER INFORMATION: "n" = a, t, g, or c.
<220> FEATURE:
<221> NAME/KEY: misc_feature
<222> LOCATION: (24)..(25)
<223> OTHER INFORMATION: "n" = a, t, g, or c.
<220> FEATURE:
<221> NAME/KEY: misc_feature
<222> LOCATION: (27)..(28)
<223> OTHER INFORMATION: "n" = a, t, g, or c.
<220> FEATURE:
<221> NAME/KEY: misc_feature
<222> LOCATION: (30)..(31)
<223> OTHER INFORMATION: "n" = a, t, g, or c.
<220> FEATURE:
<221> NAME/KEY: misc_feature
<222> LOCATION: (33)..(34)
```

```
<223> OTHER INFORMATION: "n" = a, t, g, or c.
<220> FEATURE:
<221> NAME/KEY: misc_feature
<222> LOCATION: (36)..(37)
<223> OTHER INFORMATION: "n" = a, t, g, or c.
<220> FEATURE:
<221> NAME/KEY: misc_feature
<222> LOCATION: (39)..(40)
<223> OTHER INFORMATION: "n" = a, t, g, or c.
<220> FEATURE:
<221> NAME/KEY: misc_feature
<222> LOCATION: (42)..(43)
<223> OTHER INFORMATION: "n" = a, t, g, or c.
<220> FEATURE:
<221> NAME/KEY: misc_feature
<222> LOCATION: (45)..(46)
<223> OTHER INFORMATION: "n" = a, t, g, or c.
<220> FEATURE:
<221> NAME/KEY: misc_feature
<222> LOCATION: (48)..(49)
<223> OTHER INFORMATION: "n" = a, t, g, or c.
<220> FEATURE:
<221> NAME/KEY: misc_feature
<222> LOCATION: (51)..(52)
<223> OTHER INFORMATION: "n" = a, t, g, or c.
<220> FEATURE:
<221> NAME/KEY: misc_feature
<222> LOCATION: (54)..(55)
<223> OTHER INFORMATION: "n" = a, t, g, or c.
<220> FEATURE:
<221> NAME/KEY: misc_feature
<222> LOCATION: (57)..(58)
<223> OTHER INFORMATION: "n" = a, t, g, or c.
<220> FEATURE:
<221> NAME/KEY: misc_feature
<222> LOCATION: (60)..(61)
<223> OTHER INFORMATION: "n" = a, t, g, or c.
<220> FEATURE:
<221> NAME/KEY: misc_feature
<222> LOCATION: (63)..(64)
<223> OTHER INFORMATION: "n" = a, t, g, or c.

<400> SEQUENCE: 15
gatccatgca gaattcctgc nnknnknnkn nknnknnknn knnknnknnk nnknnknnkn      60
nknnktgcaa gcttgctaca gaccat                                          86

<210> SEQ ID NO 16
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 16
gaatccatgc agaattcc                                                   18

<210> SEQ ID NO 17
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 17
atggtctgta gcaagctt                                                   18

<210> SEQ ID NO 18
<211> LENGTH: 20
<212> TYPE: DNA
<213> ORGANISM: Artificial
<220> FEATURE:
<223> OTHER INFORMATION: an artificially synthesized primer sequence
```

<400> SEQUENCE: 18
gatccatgca gaattcctgc                                              20

<210> SEQ ID NO 19
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 19
atggtctgta gcaagcttgc a                                            21

<210> SEQ ID NO 20
<211> LENGTH: 236
<212> TYPE: DNA
<213> ORGANISM: Mus musculus

<400> SEQUENCE: 20
caccaagcgt tggattgttc acccactaat agggaacgtg agctgggttt agaccgtcgt    60
gagacaggtt agttttaccc tactgatgat gtgttgttgc catggtaatc ctgctcagta   120
cgagaggaac cgcaggttca gacatttggt gtatgtgctt ggctgaggag ccaatggggc   180
gaagctacca tctgtgggat tatgactgaa cgcctctaag tcagaatccc gcccag       236

<210> SEQ ID NO 21
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 21
gctctgcggt aggtactgtt                                              20

<210> SEQ ID NO 22
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 22
cggtgcccca agaatcggt                                               20

<210> SEQ ID NO 23
<211> LENGTH: 30
<212> TYPE: PRT
<213> ORGANISM: Artificial
<220> FEATURE:
<223> OTHER INFORMATION: an artificially synthesized sequence

<400> SEQUENCE: 23

Met Leu Gly Asp Pro Asn Cys Val Lys Gln Ala Val Gln Ser Ser Val
1               5                   10                  15

Lys His Pro Asp Leu Ser Cys Lys Leu Ala Ala Ala Leu Glu
            20                  25                  30

<210> SEQ ID NO 24
<211> LENGTH: 30
<212> TYPE: PRT
<213> ORGANISM: Artificial
<220> FEATURE:
<223> OTHER INFORMATION: an artificially synthesized sequence -continued

```
<400> SEQUENCE: 24

Met Leu Gly Asp Pro Asn Cys Pro Arg Gly Leu Pro Val Thr Thr Arg
1               5                   10                  15

Leu Met Glu Lys Ser Lys Cys Lys Leu Ala Ala Ala Leu Glu
            20                  25                  30
```

POLYPEPTIDES HAVING BRAIN-LOCALIZING ACTIVITY AND USES THEREOF

TECHNICAL FIELD

The present invention relates to polypeptides having a brain-localizing activity, molecules comprising these polypeptides, and pharmaceutical agents that confer brain-localizing activity.

BACKGROUND ART

Achieving an effective concentration of a drug or such by oral administration or injection is more difficult in the brain than in other organs because of the presence of the blood-brain barrier. While an effective drug concentration may be ensured by administering a large dose, this would mean infusing the drug in excess amounts into peripheral blood, which would cause adverse effects such as kidney and liver damage. Therefore, it became necessary to develop a system that selectively transports drugs to the brain. Numerous studies are being carried out in this respect. Most of such research and development involve efforts to enhance brain localization through chemical modification of the drug itself by utilizing a property of cerebrovascular endothelial cells—the higher the lipid solubility of a substance, the more easily it passes through the blood-brain barrier. Such a method improves drug localization in the brain by several folds at best, which is on the whole, no more than an error range. In the brain, contrary to peripheral organs where substances permeate through the intercellular spaces of vascular endothelial cells, the intercellular spaces of cerebrovascular endothelial cells form special structures called tight junctions and hardly allow permeation of blood components through them. Therefore, transport of substances to the brain must be carried out by permeation after chemical modification of the substances to make them lipid-soluble and directly integratable into the cell membrane. More specifically, this method makes substances permeate directly into cells as there is no alternate route for substance transport to the brain, different from peripheral organs. However, since this mechanism is different from the usual, the efficiency is several thousands to tens of thousands times lower. Therefore, this method cannot be referred to as brain-specific drug transport.

With recent technological advances, techniques that target membrane surface proteins expressed on cerebrovascular endothelial cells have been developed. In particular, it is effective to utilize the function of proteins called transporters for incorporating drugs into the brain. Since hardly any substances permeate into the brain through intercellular spaces as described above, amino acids and sugars in blood are specifically transported into the brain by binding to transporters expressed on the blood-brain barrier. Transferrin receptors are transporter molecules that transport proteins called transferrins to the brain. Transferrins supply metal ions to metalloenzymes which are necessary for brain activity. It was reported that using specialized antibodies to target transferrin receptors could increase the brain localization of drugs by several tens to approximately a hundred times (see Non-Patent Document 1).

However, transferrin receptors are expressed not only in cerebrovascular endothelial cells, but also in liver and kidneys at an even larger quantity. Therefore, when this system is used, along with an increase in the amount of drug transported to the brain, the drug is also introduced into the liver and kidneys. Thus, this can hardly be called brain-specific transport. In addition, although there have been reports on systems that utilize several transporter molecules and antiporter molecules such as P-glycoproteins, none of them have been confirmed to be effective.

Furthermore, methods that utilize special functional peptides have been recently developed. These peptides are called PTD sequences, and were identified as peptide sequences necessary for HIV tat gene products to translocate into the cell nucleus. These peptides pass through not only the nuclear membrane, but all kinds of cell membranes (see Non-Patent Document 2), and can therefore be distributed to organs throughout the entire body when injected into blood. PTD peptides can transport substances into the brain because they can pass through the cell membrane of cerebrovascular endothelial cells. However, although both PTD sequence-mediated transfer through the cell membrane and permeation from the intercellular space are effective in peripheral organs, the latter permeation is absent in the brain, making substance permeability much lower than in other organs. Therefore, this technique also cannot be brain-specific.

Meanwhile, molecules that regulate the organ specificity of vascular endothelial cells have been recently reported. Depending on the organ's role and specificity, each organ in the body has different nutritional requirements and different degrees of requirements for various factors supplied by blood. It is gradually becoming clear that vascular endothelial cells distributed in organs have slightly different characteristics depending on where they exist. Furthermore, vascular endothelial cells serve as direct contact points with inflammatory cells and immune cells present in blood, and control the invasion of these cells during inflammation and morbid conditions. Invading cells then accumulate at lesions by recognizing inflammatory homing receptors that appear during inflammation, as well as tissue-specific vascular endothelial cell marker molecules (called cellular zip codes). Although their roles are still unclear, these cell markers are attracting attention because targeting of these molecules can at least allow targeting of a molecule of interest up to vascular endothelial cells of an organ (Non-Patent Document 3). However, although this method can target a molecule of interest up to vascular endothelial cells of each organ, systems for introducing the molecule into the parenchyma of an organ must be devised.

(Non-Patent Document 1) Ningya Shi and William M. Pardridge, Noninvasive gene targeting to the brain. Proc. Natl. Acad. Sci. USA, Vol. 97, Issue 13, 7567-7572, Jun. 20, 2000
(Non-Patent Document 2) Steven R. Schwarze, Alan Ho, Adamina Vocero-Akbani, and Steven F. Dowdy, In Vivo Protein Transduction: Delivery of a Biologically Active Protein into the Mouse. Science 1999 Sep. 3; 285: 1569-1572.
(Non-Patent Document 3) Renata Pasqualini, Erkki Ruoslahti, Organ targeting in vivo using phage display peptide libraries. Nature Vol. 380, 28, Mar. 1996.

DISCLOSURE OF THE INVENTION

The present invention was achieved under the above circumstances. An objective of the present invention is to discover factors (motif sequences) involved in brain-localizing activity. Another objective of the present invention is to provide polypeptides having brain-localizing activity, molecules comprising these polypeptides, and pharmaceutical agents that confer brain-localizing activity.

The present inventors conducted dedicated studies to solve the above-mentioned problems. Mechanisms by which cells penetrate into tissues include pathways in which cells pass through intercellular spaces (paracellular pathways) and pathways in which cells pass through cells (transcellular pathways). The latter pathways are assumed to occur under specific conditions. When studying the phenomenon of a particular type of cell (microglia) that enters the brain without destroying the blood-brain barrier, the present inventors discovered that this cell has a molecule that induces the transcellular pathway (Sawada, M., Imai, F., Suzuki, H., Hayakawa, M., Kanno, T., Nagatsu, T. FEBS Lett, 433: 37-40, 1998. Brain-specific gene expression by immortalized microglial cell-mediated gene transfer in the mammalian brain).

The present inventors arrived at the idea that peptide fragments of the active site of such a molecule can be used to enable brain-specific targeting and transport of substances that have so far been impossible.

Ligand molecules that induce the above-mentioned mechanism are thought to exist in microglias. Thus, the present inventors successfully isolated and identified molecules of interest by separating mRNAs from microglias, preparing a cDNA library, incorporating the library into T7 phages, and screening for phages that expressed brain-localizing activity.

Furthermore, the present inventors synthesized DNAs that encode polypeptides comprising random amino acid sequences, incorporated them into a phage library, and screened for polypeptides that have brain-localizing activity.

As a result, the present inventors obtained several polypeptides having brain-localizing activity, and successfully discovered amino acid motif sequences that are thought to be involved in brain-localizing activity and their sequence characteristics.

Furthermore, the present inventors administered synthetic polypeptides comprising the above-mentioned motif sequences to test animals and confirmed that these polypeptides indeed have an activity to translocate into the brain. The present inventors also conducted dedicated studies to elucidate the mechanism by which the polypeptides of this invention translocate into the brain, and showed that the polypeptides are translocated into brain tissues by a transmigration mechanism (transcellular pathway). More specifically, the peptides of the present invention are also very useful as molecules that confer transmigration-inducing ability.

Polypeptides comprising an amino acid motif sequence of the present invention, or characteristic amino acids thereof, may have brain-localizing activity. Furthermore, the present inventors showed that molecules to which these polypeptides have been attached have brain-localizing activity, even if they are large molecules like phage particles. Polypeptides comprising a motif sequence discovered by the present inventors can be attached to arbitrary molecules to confer brain-localizing activity on these molecules. Therefore, polypeptides comprising the motif sequence may become brain-localizing activity-conferring pharmaceutical agents.

As described above, the present inventors succeeded in solving the above-mentioned problems and thereby completed the present invention. Namely, the present invention relates to polypeptides having brain-localizing activity, molecules comprising these polypeptides, and pharmaceutical agents that confer brain-localizing activity. More specifically, the present invention provides:

[1] a polypeptide (brain-localizing polypeptide) having brain-localizing activity, wherein 10% or more of the polypeptide is comprised of basic amino acid residues (K or R);

[2] a polypeptide having brain-localizing activity, wherein the polypeptide comprises a cyclic peptide region, and wherein 10% or more of the cyclic peptide region is comprised of basic amino acid residues (K or R);

[3] a polypeptide having brain-localizing activity, wherein the polypeptide comprises a cyclic peptide region and at least one or more basic amino acid residues (K or R) in the cyclic peptide region;

[4] a polypeptide having brain-localizing activity, wherein the polypeptide comprises a cyclic peptide region and at least one or more basic amino acid residues (K or R), and wherein 80% or more of the remaining amino acid residues in the cyclic region are selected from the following group of amino acid residues:

G, A, V, L, S, T, P, Q, H, and N;

[5] a polypeptide having brain-localizing activity, wherein the polypeptide comprises the amino acid motif sequence of:

$X_1$—(R or K)—$X_3$—$X_4$ or $X_4$—$X_3$—(R or K)—$X_1$, wherein $X_1$ denotes S, T, N, P, V, or L; $X_3$ denotes an arbitrary amino acid; and $X_4$ denotes G, S, T, C, N, L, Q, or Y;

[6] the polypeptide of any one of [2] to [4], wherein the cyclic peptide region comprises the amino acid motif sequence of [5];

[7] the polypeptide of [5] or [6], wherein the amino acid motif sequence is:

$X_1$—(R or K)—$X_3$—$X_4$ or $X_4$—$X_3$—(R or K)—$X_1$, wherein $X_1$ denotes S, T, N, P, or V; $X_3$ denotes an arbitrary amino acid; and $X_4$ denotes an uncharged polar amino acid (G, S, T, C, N, Q, or Y);

[8] the polypeptide of [5] or [6], wherein the amino acid motif sequence is:

$X_1$—(R or K)—$X_3$—$X_4$ or $X_4$—$X_3$—(R or K)—$X_1$, wherein $X_1$ denotes S, T, P, or L; $X_3$ denotes an arbitrary amino acid; and $X_4$ denotes S, T, C, L, or Q;

[9] the polypeptide of any one of [1] to [8], wherein the polypeptide has transmigration-inducing activity;

[10] the polypeptide of any one of [1] to [8], wherein the polypeptide has activity to bind to a cerebrovascular endothelial cell;

[11] a polypeptide of any one of (a) to (c) described below:

(a) a polypeptide comprising the amino acid sequence of any one of SEQ ID NOs: 1 to 12, (b) a polypeptide comprising a peptide region cyclized by a disulfide bond formed between cysteine residues on both ends of the polypeptide of (a), and (c) a polypeptide having brain-localizing activity, and comprising an amino acid sequence with one or several amino acid additions, deletions, or substitutions in the amino acid sequence of any one of SEQ ID NOs: 1 to 12;

[12] the polypeptide of any one of [1] to [11], wherein the length of the polypeptide is 9 amino acids or less;

[13] a polynucleotide encoding the polypeptide of any one of [1] to [12];

[14] an antibody that binds to the polypeptide of any one of [1] to [12];

[15] a pharmaceutical agent for conferring brain-localizing activity to an arbitrary molecule, wherein the agent comprises the polypeptide of any one of [1] to [12];

[16] the pharmaceutical agent of [15], wherein the arbitrary molecule is an arbitrary polypeptide;

[17] a molecule having brain-localizing activity, wherein the molecule comprises the polypeptide of any one of [1] to [12];

[18] the molecule of [17], wherein the molecule is a phage particle or a coat protein of a phage particle;

[19] the molecule of [17], wherein the molecule is a fusion protein formed with the polypeptide of any one of [1] to [12];

[20] a carrier for delivery to the brain, wherein the carrier comprises the polypeptide of any one of [1] to [12];

[21] a carrier for delivery to the brain, wherein the carrier comprises a structure in which the polypeptide of any one of [1] to [12] is bound to a micelle, liposome, or microcapsule;

[22] a therapeutic agent for brain disease, wherein the agent comprises a structure in which a drug is supported by the carrier of [20] or [21];

[23] a method for producing a molecule having brain-localizing activity, wherein the method comprises binding the polypeptide of any one of [1] to [12] to an arbitrary molecule;

[24] a method for producing a protein molecule having brain-localizing activity, wherein the method comprises the steps of:

(a) preparing an expression vector comprising a DNA in an expressible manner, wherein the DNA has a structure in which a DNA encoding an arbitrary protein molecule is linked to a DNA encoding the polypeptide of any one of [1] to [12], (b) introducing the expression vector into a cell, and (c) collecting an expression product of the vector;

[25] a method for translocating an arbitrary molecule into the brain of a non-human animal, wherein the method comprises the steps of:

(a) producing a molecule having brain-localizing activity, wherein the molecule comprises a structure in which an arbitrary molecule is bound to the polypeptide of any one of [1] to [12], and (b) administering the molecule into the body of the non-human animal;

[26] a method of screening for a molecule having binding activity to the polypeptide of any one of [1] to [12], wherein the method comprises the steps of:

(a) contacting the polypeptide of any one of [1] to [12] with a test molecule, (b) detecting binding activity between the polypeptide and the test molecule, and (c) selecting a molecule that binds to the polypeptide;

[27] a method of screening for a polypeptide having brain-localizing activity, wherein the method comprises the steps of:

(a) preparing a phage particle displaying a test polypeptide on its phage coat protein, (b) administering the phage particle to a non-human animal, (c) collecting a phage particle from a brain tissue of the non-human animal, and (d) selecting a test polypeptide displayed on the phage particle collected in step (c) as a polypeptide having brain-localizing activity;

[28] the method of [27], wherein the test polypeptide comprises the amino acid motif sequence of any one of [5], [7], and [8];

[29] the method of [27], wherein the phage is M13 phage or T7 phage; and

[30] the method of [27], wherein the method further comprises selecting a phage particle that binds to a crebrovascular endothelial cell subsequent to step (a).

The present invention provides polypeptides having brain-localizing activity. In general, translocation of substances from blood into brain tissues is restricted by a structure called the blood-brain barrier (BBB). This structure protects the brain from harmful substances. In the present invention, "brain-localizing activity" refers to the activity of molecules, such as polypeptides administered to the body (for example, by intravenous administration), to translocate into brain tissues. The polypeptides of the present invention can be ordinary polypeptides having brain-localizing activity (brain-localizing polypeptides), but they can also be, for example, polypeptides having the ability to pass through the blood-brain barrier or to induce transmigration (transcytosis). The polypeptides of the present invention can be attached to other substances (molecules) to translocate them into the brain. Therefore, the polypeptides of the present invention can be referred to as "polypeptides that confer brain-localizing activity", "brain-localizing peptide tags", or "agents that confer brain-localizing activity".

Furthermore, the present inventors revealed that 9-amino acid polypeptides can confer effective brain-localizing activity to other substances (molecules). Therefore, at the least, it can be said that polypeptides as short as 9 amino acids can confer effective brain-localizing activity to other molecules. The length of the polypeptides of the present invention is not particularly limited, but is for example, 100 amino acids or less, preferably 15 amino acids or less, more preferably 9 amino acids or less, and most preferably 4 to 9 amino acids.

Polypeptides comprising one of the following sequences were found to have brain-localizing activity through experiments demonstrated in the Examples described later.

TABLE 1

| Name | Amino acid sequence | |
|---|---|---|
| T2J001 | CSNLLSRHC | (SEQ ID NO: 1) |
| T2J002 | CSLNTRSQC | (SEQ ID NO: 2) |
| T2J003 | CVAPSRATC | (SEQ ID NO: 3) |
| T2J004 | CVVRHLQQC | (SEQ ID NO: 4) |
| T2J004V3L | CVLRHLQQC | (SEQ ID NO: 5) |
| T2J006 | CRQLVQVHC | (SEQ ID NO: 6) |
| T2J007 | CGPLKTSAC | (SEQ ID NO: 7) |
| T2J008 | CLKPGPKHC | (SEQ ID NO: 8) |
| T2J009 | CRSPQPAVC | (SEQ ID NO: 9) |
| T2J012 | CNPLSPRSC | (SEQ ID NO: 10) |
| T2J013 | CPAGAVKSC | (SEQ ID NO: 11) |
| T2J013V6L | CPAGALKSC | (SEQ ID NO: 12) |

In a preferred embodiment, the polypeptides of the present invention comprise the amino acid motif sequence of [Sequence 1], more preferably the amino acid motif sequence of [Sequence 2], or the amino acid motif sequence of [Sequence 3] described below. In other words, a preferred embodiment of the present invention provides polypeptides comprising at least any one of the amino acid motif sequences of [Sequence 1] to [Sequence 3] shown below.

$X_1$—(R or K)—$X_3$—$X_4$ or $X_4$—$X_3$—(R or K)—$X_1$,    [Sequence 1]

wherein $X_1$ denotes S (serine), T (threonine), N (asparagine), P (proline), V (valine), or L (leucine);

X₃ denotes an arbitrary amino acid; and

X₄ denotes G (glycine), S (serine), T (theonine), C (cysteine), N (asparagine), L (leucine), Q (glutamine), or Y (tyrosine).

$$X_1\text{—(R or K)—}X_3\text{—}X_4 \text{ or}$$

$$X_4\text{—}X_3\text{—(R or K)—}X_1, \quad \text{[Sequence 2]}$$

wherein

X₁ denotes S (serine), T (threonine), N (asparagine), P (proline), or V (valine), and is preferably S or T;

X₃ denotes an arbitrary amino acid; and

X₄ denotes G (glycine), S (serine), T (threonine), C (cysteine), N (asparagine), Q (glutamine), or Y (tyrosine), and is more preferably T, Q, or C. In the above-mentioned (R or K), R is more preferable.

These amino acids (G, S, T, C, N, Q, and Y) are generally categorized into uncharged polar amino acids.

$$X_1\text{—(R or K)—}X_3\text{—}X_4 \text{ or}$$

$$X_4\text{—}X_3\text{—(R or K)—}X_1, \quad \text{[Sequence 3]}$$

wherein

X₁ denotes S (serine), T (threonine), P (proline), or L (leucine);

X₃ denotes an arbitrary amino acid; and

X₄ denotes G (glycine), S (serine), T (threonine), C (cysteine), L (leucine), or Q (glutamine).

Herein, the amino acids are described using the conventional single letter code (for example, R for arginine and K for lysine). Furthermore, the amino acid sequences are written in the order from N terminus to C terminus according to conventional description methods.

The present inventors discovered that polypeptides having a structure in which the above-mentioned peptides are cyclized (more specifically, cyclized through a disulfide bond (S—S bond) formed between cysteines at the ends of the peptides) show higher brain-localizing activity.

Therefore, in a preferred embodiment, the polypeptides of the present invention have cyclic structures. In the present invention, a motif sequence described above can be found in the polypeptides that constitute such a cyclic region. Amino acids that constitute the motif sequences consist of four neighboring amino acid residues. These neighboring amino acids usually form peptide bonds with each other, but when they are cysteine residues, disulfide bonds may be formed. "Four neighboring amino acid residues" in the motif sequences of the present invention are not limited to those that bind to each other via peptide bonds, and may also form disulfide bonds when the neighboring amino acids are cysteines. More specifically, the symbol "–" in the above-mentioned [Sequence 1] to [Sequence 3] generally refers to a peptide bond, but when the neighboring amino acids are cysteines, "–" may refer to a disulfide bond (S—S bond). For example, even if the motif sequences of the present invention are not found on the amino acid sequences of straight-chain polypeptides, the motifs of the present invention may be formed by amino acids that become neighbors as a result of cyclic structure formation.

Furthermore, in a preferred embodiment of the present invention, as long as a polypeptide comprises an above-mentioned motif sequence consisted of 4 amino acids, the non-motif amino acid sequence of the polypeptide is not particularly limited.

The polypeptides having brain-localizing activity described in Table 1 have the following characteristics.

In the polypeptide regions that may form a cyclic structure (more specifically, the amino acid sequences excluding the cysteines at both ends), (1) all polypeptides comprise a basic amino acid, K or R, and (2) the remaining amino acid residues consist of any of the 10 amino acids [G, A, V, L, S, T, P, Q, H, and N].

Therefore, a preferred embodiment of the present invention provides polypeptides having brain-localizing activity, polypeptides comprising a cyclic region in which at least one or more basic amino acid residues (K or R) are present, and the remaining amino acid residues (usually 80% or more, preferably 85% or more, more preferably 90% or more, even more preferably 95% or more, and most preferably 100%) are selected from the group of amino acid residues [G, A, V, L, S, T, P, Q, H, and N] (this characteristic may be referred to herein as "Feature 1"). In a more preferable embodiment of the present invention, polypeptides have the above-mentioned "Feature 1" and comprise a motif sequence ([Sequence 1] to [Sequence 3]) of the present invention.

Furthermore, as described above in "Feature 1", all of the polypeptides of the present invention were found to comprise a basic amino acid (K or R). For example, in the 9-amino acid polypeptides used in Examples, at least one basic amino acid was found (content in terms of the total amino acids is ⅑=0.11 (11%) or more).

Therefore, in an embodiment of the present invention, the following peptides are provided:

(a) a polypeptide having brain-localizing activity, in which the polypeptide comprises 10% or more basic amino acid residues (K or R);

(b) a polypeptide having brain-localizing activity, in which the polypeptide comprises a cyclic peptide region and 10% or more basic amino acid residues (K or R) in the cyclic peptide region; and (c) a polypeptide having brain-localizing activity, wherein the polypeptide comprises a cyclic peptide region and at least one or more basic amino acid residues (K or R) in the cyclic peptide region.

The upper limit of the length of the polypeptides of the present invention is not particularly limited. Typically, polypeptides that are 7 amino acids or longer and comprise a 4 amino acid sequence motif or the aforementioned "Feature 1" are considered to have effective brain-localizing activity. Although there is no upper limit on the length, polypeptides with a length of 50 amino acids or less, or preferably 35 amino acids or less are generally considered to have a sufficient brain-localizing activity. Furthermore, since even long polypeptides comprising these polypeptides generally have brain-localizing activity, the length of the polypeptides of the present invention is not limited.

In a preferred embodiment of the present invention, the length of a polypeptide region to be cyclized is not particularly limited. In an experiment, the present inventors used a 9-amino acid residue polypeptide comprising cysteine residues at both ends as an example of the peptide to be cyclized. More specifically, for example, polypeptides comprising a cyclic structure that has a length of 10 amino acids or more are thought to have brain-localizing activity as long as they have a motif sequence of the present invention or "Feature 1". Therefore, without limitation, the length of the cyclic peptide region in a polypeptide of the present invention is, for example, 100 amino acids or less, preferably 50 amino acids or less, more preferably 4 to 30 amino acids, even more preferably 4 to 15 amino acids, yet even more preferably 4 to 9 amino acids, and most preferably 4 to 7 amino acids.

Furthermore, in a preferred embodiment, the polypeptides of the present invention comprise function (activity) (A) and/or (B) below:
(A) transmigration (transcytosis)-inducing activity
(B) cerebrovascular endothelial cell-binding activity.

The term "transmigration" in (A) refers to a phenomenon in which certain molecules penetrate into the brain by passing through vascular endothelial cells rather than intercellular spaces of the vascular endothelial cells. This is called "transendothelial cell migration", "transcellular pathway", or "transcytosis". The molecules (cells and such) that pass through vascular endothelial cells by this mechanism may have signal molecules on their surface and induce the above-mentioned phenomenon in the vascular endothelial cells through receptors on the surface of these cells (FIG. 1).

The polypeptides of the present invention may have an activity to induce transmigration in vascular endothelial cells. More specifically, the polypeptides of the present invention may serve as signal molecules for inducing transmigration.

Signal molecules are thought to bind to cerebrovascular endothelial cells (for example, receptors on the cells) in the early stages of transmigration. Therefore, in a preferred embodiment, one of the characteristics of the polypeptides of the present invention is to have an activity to bind to cerebrovascular endothelial cells.

Whether an arbitrary test molecule has the transmigration-inducing activity of (A) or whether it has the cerebrovascular endothelial cell-binding activity of (B) can be evaluated appropriately using methods known to those skilled in the art. As an example, the evaluation can be carried out by administering a fluorescence-labeled test molecule into blood vessels, and then observing frozen cross-sections of cerebrovascular endothelial cells under a fluorescence microscope. For example, if vascular endothelial cells to which a fluorescence-labeled test molecule is attached are observed, the test molecules are judged to have the activity of (B), and if the fluorescence-labeled test molecules are detected within the vascular endothelial cells, the test molecules are judged to have the activity of (A).

In addition to the fluorescence-labeling method, also included are methods using isotope labels or PET ligand labels, detection methods using MRI after binding with a magnetite or the like, etc. Besides the above-mentioned in vivo methods, other embodiments include methods of evaluating transmigration-inducing activity by inducing a blood-brain barrier (BBB) in a vascular endothelial cell culture, and then administering the above-mentioned test molecule. If the molecule is confirmed to permeate through the BBB, it is judged to have the activity of (A), and if the molecule is adhered to the vascular endothelial cells after washing, it is judged to have the activity of (B).

Furthermore, the phrase "cerebrovascular endothelial cells" in the present invention can refer to cells such as mouse MBEC4, commercially available human cerebrovascular endothelial cell BBEC, primary cultured bovine cerebrovascular endothelial cells, or co-cultures of peripheral blood vessel-derived vascular endothelial cells and astrocytes prepared for inducing a BBB-like function.

Those skilled in the art can use these cells to evaluate the activity of (A) or (B) in arbitrary polypeptides (synthetic peptides), or molecules comprising these peptides.

Specifically, the activities can be suitably evaluated by the methods described in the following Examples.

More specifically, the polypeptides of the present invention may include polypeptides comprising the amino acid sequences described in Table 1. However, these are only some examples, and the polypeptides of the present invention are not limited thereto. The present inventors demonstrated that polypeptides comprising an amino acid sequence in Table 1, or phage molecules expressing one of these polypeptides on their coat proteins, indeed have brain-localizing activity as demonstrated later in Examples.

Therefore, the present invention provides any one of the polypeptides of (a) to (c) described below:
(a) a polypeptide comprising the amino acid sequence of any one of SEQ ID NOs: 1 to 12;
(b) a polypeptide comprising a peptide region cyclized through a disulfide bond formed between cysteine residues at both ends of the polypeptide of (a); and
(c) a polypeptide having brain-localizing activity, and comprising an amino acid sequence with one or several amino acid additions, deletions, or substitutions in the amino acid sequence of any one of SEQ ID NOs: 1 to 12.

In the polypeptide of (c), amino acid additions, deletions or substitutions preferably occur in the non-motif sequence amino acid residues of the present invention ([Sequence 1] to [Sequence 3]), and/or preferably occur such that the polypeptide has "Feature 1" of the present invention. Furthermore, "several" generally refers to a number within the range of 2 to 9.

Organisms in which the polypeptides of this invention show brain-localizing activity are not particularly limited as long as they are animals that have a blood-brain barrier, but are usually mammals, and preferably mice, rats, gerbils, cats, cattle, monkeys, or humans.

The polypeptides of the present invention may be polypeptides derived from natural proteins, polypeptides derived from recombinant proteins, chemically synthesized polypeptides, or such. Those skilled in the art can synthesize polypeptides comprising any amino acid sequence. For example, synthesis of polypeptides such as those comprising an above-mentioned motif sequence and/or "Feature 1" can be carried out suitably by using methods known to those skilled in the art, for example, methods that use a commercially available polypeptide synthesizer.

Furthermore, polynucleotides encoding the polypeptides of the present invention are also comprised in this invention. The polynucleotides generally include both DNAs and RNAs. More specifically, DNAs encoding the polypeptides of the present invention, and RNAs that are transcription products of these DNAs are encompassed in the present invention.

The present invention provides vectors into which the polynucleotides of the present invention have been inserted, host cells carrying the polynucleotides or the vectors of the present invention, and methods for producing the polypeptides of the present invention using the host cells.

The vectors of the present invention are not particularly limited as long as the inserted DNA is stably maintained. For example, when using *E. coli* as host, the cloning vector is preferably a pBluescript vector (Stratagene) and such. Expression vectors are particularly useful as vectors for producing the polypeptides of the present invention. Expression vectors are not particularly limited as long as they can express polypeptides in test tubes, *E. coli,* cultured cells, or individual organisms. For example, preferred vectors are pBEST vector (Promega) for expression in test tubes, pET vector (Invitrogen) for *E. coli,* pME18S-FL3 vector (GenBank Accession No. AB009864) for cultured cells, pME18S vector (Mol. Cell Biol. 8:466-472(1988)) for individual organisms. Insertion of a DNA of the present invention into vectors can be performed by standard methods such as ligase reactions using restriction enzyme sites (Current protocols in Molecular Biology edit. Ausubel et al. (1987) Publish. John Wiley & Sons. Section 11.4-11.11).

The host cells into which a vector of the present invention is introduced are not particularly limited, and various host cells can be used depending on the purpose. Cells used for expressing the polypeptides include bacterial cells (for example, *Streptococcus, Staphylococcus, E. coli, Streptomyces,* and *Bacillus subtilis*), fungal cells (for example, yeast and *Aspergillus*), insect cells (for example, *Drosophila* S2 and *Spodoptera* SF9), animal cells (for example, CHO, COS, HeLa, C127, 3T3, BHK, HEK293, Bowes melanoma cell), and plant cells. Vectors can be introduced into host cells using known methods such as the calcium phosphate precipitation method, electroporation method (Current protocols in Molecular Biology edit. Ausubel et al. (1987) Publish. John Wiley & Sons. Section 9.1-9.9), lipofectamine method (GIBCO-BRL), and microinjection method.

For secreting host cell-expressed polypeptides into the lumen of endoplasmic reticulum, periplasmic space, or extracellular environment, suitable secretion signals can be incorporated into the polypeptides of interest. These signals may be intrinsic or foreign to the polypeptides of interest.

When the polypeptides of the present invention are secreted into culture media, they are collected by harvesting the media. When the polypeptides of the present invention are produced inside cells, the cells are lysed to collect these polypeptides.

The polypeptides of the present invention can be collected and purified from recombinant cell cultures by known methods including ammonium sulfate or ethanol precipitation, acidic extraction, anion or cation exchange chromatography, phosphocellulose chromatography, hydrophobic interaction chromatography, affinity chromatography, hydroxyapatite chromatography, and lectin chromatography.

Since the polypeptides of the present invention have brain-localizing activity, molecules to which these polypeptides bind are also expected to have brain-localizing activity. The present inventors demonstrated that phage particles which normally do not have brain-localizing activity had indeed acquired such an activity when a polypeptide of the present invention was incorporated into their coat proteins. Therefore, the polypeptides of the present invention are thought to confer brain-localizing activity to arbitrary molecules by binding to these molecules. More specifically, the polypeptides of the present invention are useful in that they can confer brain-localizing activity to other molecules. The present invention provides pharmaceutical agents that comprise a polypeptide of the present invention for conferring brain-localizing activity to arbitrary molecules. In a preferred embodiment, peptide tags for translocating arbitrary molecules into the brain are provided, wherein the tags comprise an above-mentioned amino acid motif sequence and/or a polypeptide comprising the above-mentioned "Feature 1".

Examples of the peptide tags of the present invention include conjugate molecules formed between the peptides of the present invention and biotin, which are described later in the Examples. Such conjugate molecules can be linked appropriately with any avidin-conjugated molecule. More specifically, brain-localizing peptide-conjugate molecules having a structure such as that shown in FIG. 8, or conjugate molecules specifically used in the following Examples are comprised in the present invention as preferred embodiments. By using these conjugate molecules, desired avidin-conjugated molecules can be translocated into the brain. Methods of translocating any molecule into the brain by using these conjugate molecules are also encompassed in the present invention. Furthermore, the present invention comprises molecules that have been conferred with a brain-localizing activity by a pharmaceutical agent of the present invention mentioned above.

Molecules that are conferred with a brain-localizing activity by the polypeptides (pharmaceutical agents) of the present invention are not particularly limited, and include: single compounds such as natural compounds, organic compounds, inorganic compounds, carbohydrate chains, proteins, and peptides; as well as compound libraries, expression products of gene libraries, cells, cell extracts, cell culture supenatants, microorganisms, products of microorganisms, phages, antigens, antibodies, micelles (polymeric micelles and such), liposomes, microcapsules, peptide nucleic acids (PNAs), and pharmaceutical compounds. The polypeptides of the present invention or the aforementioned molecules can be appropriately labeled if necessary. The labels include radioactive labels, fluorescence labels, and enzyme labels.

The size of the molecules that are conferred with a brain-localizing activity by the polypeptides of the present invention is not particularly limited, but the maximum size is generally a size that allows the molecules to physically pass through the blood-brain barrier. As demonstrated by the Examples, molecules with the size of a standard phage can pass through the blood-brain barrier via the action of the polypeptides of the present invention. Therefore, these molecules (substances) may have sizes similar to that of a phage. For example, if the molecules to be conferred with brain-localizing activity are made up of amino acids, they may comprise around 100,000 amino acids.

Those skilled in the art can use known methods to suitably bind an above-mentioned molecule to a polypeptide of the present invention according to the type of the molecule.

For example, the molecules and polypeptides of the present invention can be linked by methods that use commercially available coupling reagents (N-binding type, COOH-binding type, amino acid residue modifying type, S—S linkage type, and so on), methods using chloramine T, methods that introduce isothiocyanate groups, and such.

Furthermore, when the molecule is a protein, the molecule to which a polypeptide of the present invention is linked can be prepared by using DNAs that encode a fusion protein between the protein and the polypeptide of the present invention.

More specifically, such a molecule can be produced by methods comprising the following steps:

(a) preparing an expression vector comprising a DNA in an expressible manner, wherein the DNA has a structure in which a DNA encoding an arbitrary protein molecule is linked to a DNA encoding a polypeptide of the present invention;

(b) introducing the expression vector into a cell; and (c) collecting expression products of the vector.

The present invention also provides carriers for delivery to the brain, wherein the carriers comprise a polypeptide of the present invention having brain-localizing activity. These carriers may also be referred to as "supports" or "transporters". In the present invention, the polypeptides having brain-localizing activity are themselves examples of such carriers. More specifically, by directly linking a polypeptide of the present invention to a molecule to be translocated to the brain, the molecule can be delivered to the brain. Furthermore, a preferred embodiment of the carriers of the present invention includes carriers comprising a structure in which a polypeptide of the present invention is bound to a micelle (polymeric micelle), liposome, or microcapsule.

Furthermore, by using the carriers of the present invention, desired pharmaceutical agents can be translocated to the brain. For example, by using a carrier to support a compound (pharmaceutical composition) that has a therapeutic effect on a brain disease, the compound can be delivered efficiently to the brain and exert powerful therapeutic effects. Carriers used to support a compound (pharmaceutical composition) are themselves expected to be therapeutic agents for brain diseases. Accordingly, the present invention provides therapeutic agents for brain diseases, comprising a structure in which a drug is supported on a present invention's carrier for delivery to the brain. "Supported" may refer to conditions in which a drug is directly bound to a carrier, or conditions in which a drug (pharmaceutical composition) is contained within a carrier.

In addition, the present invention provides methods for producing molecules having brain-localizing activity of the present invention. In a preferred embodiment of the present invention, the method for producing molecules having brain-localizing activity comprises binding a polypeptide of the present invention to an arbitrary molecule. When the molecules are proteins, the present invention provides production methods comprising the above-mentioned steps (a) to (c) as a preferred embodiment.

Moreover, it is preferable that the polypeptides of the present invention for binding to molecules to be conferred with brain-localizing activity are positioned on the outside of these molecules. More specifically, it is desirable that the polypeptides of the present invention are bound to the molecules in such a way that the polypeptides are positioned on the surface of the molecules.

In a preferred embodiment of the present invention, the polypeptides of the present invention include polypeptides comprising a sequence in which cysteine residues (C) are positioned on both ends of an above-mentioned motif. The SH groups of the two cysteine residues in the polypeptides are generally crosslinked (disulfide bonded) by autoxidation. A polypeptide chain comprising the motif sequence positioned between two cysteine residues as described above is expected to form a loop-shaped protrusion upon formation of a crosslink between these two cysteines. That is, by introducing the above-mentioned cysteine residues into the polypeptides of the present invention, the polypeptides can be efficiently positioned on the surface (outside) of the molecules. Other methods for positioning the polypeptides of the present invention on the outside include: recombinant production methods that position a polypeptide of the present invention on the externally exposed domain of a protein molecule to which the polypeptide chain is to be introduced; methods that bind a crosslinking agent such as PEG with a protein, lipid, synthetic carrier or such, and link a polypeptide chain to the end of the PEG chain; and methods that chemically bind a polypeptide chain to the surface of a carrier.

Examples of molecules to be bound to the polypeptides of the present invention include compounds that are desirable for direct translocation into brain tissues for brain disease treatment. These compounds are conferred with brain-localizing activity by the polypeptides of the present invention. Consequently, when these compounds are administered into a body, they are expected to translocate efficiently into brain tissues and exert therapeutic effects.

The present invention comprises the above-described molecules which have brain-localizing activity and potential therapeutic effects on brain diseases, and pharmaceutical agents comprising these molecules.

Polypeptides of the present invention having brain-localizing activity can be applied to the following cases as a therapeutic strategy for treating cranial nerve diseases.

1) Replacement Therapies that Supplement Enzymes and Bioactive Proteins Whose Amounts and Activities Have Decreased Due to Deletions or Mutations These therapies are performed on various brain diseases caused by deficiencies of particular enzymes or proteins in the brain due to genetic deletions or mutations, by injecting cells carrying genes of the deficient proteins and enzymes. For degenerative loss of particular nerve cells in Parkinson's disease and Alzheimer's disease, genes that promote synthesis of neurotransmitters which become deficient due to the degenerative loss of nerves may be used; for example, genes of enzymes involved in dopamine biosynthesis including tyrosine hydroxylase and biopterin synthase may be used for Parkinson's disease.

2) Protective Therapies for Protecting Nerve Cells that Would Otherwise be Lost by Degeneration or Such and for Strengthening Their Functions These therapies are performed by injecting cells expressing genes of neurotrophic factors, such as NGF, BDNF, GDNF, and NT3 (recent findings show that BDNF and GNNF are particularly effective for Parkinson's disease), which suppress nerve cell death by various causes including degenerative diseases and cerebral ischemia, and promote the regeneration of neurites. Furthermore, therapies for diseases that involve immune cells, such as multiple sclerosis, are performed by introducing cells that express the genes of TGF-β or IL-10, which have immunosuppressive effects.

3) Methods for Removing Tumors, Blood Clots and Such

These methods are performed by expressing factors that have antitumor effects, or by transferring cells that carry an antitumor agent into the brain. For removal of blood clots, fibrinolytic enzymes can be expressed.

4) Methods for Introducing Effective Drugs Exclusively Into the Brain

Among drugs that act on the nervous system, some have high peripheral toxicity, some act on the peripheral nervous system, and others cannot easily pass through the blood-brain barrier; therefore, drug delivery systems that are specific for the brain are necessary. Using the polypeptides of the present invention, drugs may be administered specifically to the brain, with little effect on peripheral organs.

5) Use as a Brain Disease Prevention System

Microglias are originally cells that gather at degenerated or inflamed sites to remove dead cells and are involved in damage repair. They also have antitumor effects and antiviral effects and can thus be referred to as an intracerebral defense system. Therefore, by strengthening these properties through genetic engineering and such, microglias can be applied not only to treatment for a single disease, but also to preventive measures against various diseases by strengthening the intracerebral defense system itself.

A pharmaceutical agent of the present invention may comprise only a polypeptide of the present invention, or a molecule that comprises the polypeptide and has brain-localizing activity; or may be formulated using a known pharmaceutical preparation method. For example, the agent can be formulated into a pharmaceutical formulation suitable for effective administration into the body, such as an injection (preferred), transnasal formulation, transdermal formulation, or oral agent, by suitably combining with an appropriate conventionally used carrier or vehicle, such as sterilized water, physiological saline, vegetable oil (for example, sesame oil and olive oil), coloring agent, emulsifier (for example, cholesterol), suspending agent (for example, gum arabic), surfactant (for example, polyoxyethylene hardened castor oil surfactants), solubilizing agent (for example, sodium phosphate), stabilizer (for example, sugars, sugar alcohols, and albumin), or preservative (for example, paraben). For example, injection formulations can be provided as freeze-dried products, solutions for injections, or such.

Furthermore, administration into the body can be carried out, for example by intraarterial injection, intravenous injection, or subcutaneous injection, and also intranasally, transbronchially, intramuscularly, or orally by methods known to those skilled in the art. Among these, intraarterial administration is preferred.

In addition, the present invention comprises molecules that have been conferred with brain-localizing activity by the pharmaceutical agents of the present invention. For example, phages expressing a polypeptide of the present invention on their coat proteins are preferred.

There are no particular limitations on the phages, but preferred examples include T7 phages and M13 phages. When using T7 phages, the polypeptides of the present invention can be displayed on the outside of the coat proteins called capsids.

The present invention relates to antibodies that bind to (or preferably, specifically bind to) a polypeptide(s) of the present invention. Herein, the term "antibodies" include polyclonal and monoclonal antibodies, chimeric antibodies, single-chain antibodies, humanized antibodies, and Fab or Fab fragments comprising other immunoglobulin expression library products.

A polypeptide of the present invention or cells expressing it can be used as an immunogen for producing an antibody that binds to this polypeptide. The antibody is preferably immunospecific to the polypeptide of the present invention. The term "immunospecific" means that the antibody has substantially higher affinity for the polypeptide of the present invention than for other polypeptides.

Antibodies that bind to a polypeptide of the present invention can be prepared by methods known to those skilled in the art. Polyclonal antibodies can be obtained, for example, as follows. The polypeptides of the present invention or their GST fusion proteins are used to immunize small animals such as rabbits, and their sera are collected. The antibodies are prepared by purifying these sera using ammonium sulfate precipitation, protein A or protein G column chromatography, DEAE ion exchange chromatography, affinity chromatography with columns to which the polypeptides of the present invention have been coupled, and such. For monoclonal antibody preparation, for example, a polypeptide of the present invention is used to immunize small animals such as mice, their spleens are removed and homogenized to separate the cells, and the cells are fused with mouse myeloma cells using reagents such as polyethylene glycol. From the resulting fused cells (hybridomas), clones producing an antibody that binds to the polypeptide of the present invention are selected. Next, the obtained hybridomas are transplanted into the abdominal cavities of mice, ascites are collected from these mice, and the monoclonal antibody can be prepared by purifying the obtained ascites using ammonium sulfate precipitation, protein A or protein G column chromatography, DEAE ion exchange chromatography, chromatography with affinity columns to which the polypeptide of the present invention is coupled, and such.

The antibodies of the present invention can be used to isolate, identify, and purify the polypeptides of the present invention or cells expressing these polypeptides. The polypeptides of the present invention can be used suitably in methods of screening for molecules having binding activity to the polypeptides of the present invention as described below.

The present invention provides methods of screening for molecules having binding activity to the polypeptides of the present invention. In a preferred embodiment, the methods of the present invention comprise the steps of:

(a) contacting a polypeptide of the present invention with test molecules;

(b) detecting binding activity between the polypeptide and the test molecules; and (c) selecting molecules that bind to the polypeptide.

For example, a receptor whose ligand is a polypeptide of the present invention may be obtained by the screening methods of the present invention. Such receptors are expected to be involved in transmigration in cerebrovascular endothelial cells. Functional analyses on receptors obtained by the screening methods of the present invention are expected to contribute to the elucidation of the transmigration mechanism. The screening methods of the present invention are also very useful in obtaining molecules involved in endothelial cell adhesion.

Usually, the "contacting" mentioned in step (a) is suitably carried out according to the conditions of the polypeptides of the present invention. For example, if the polypeptides of the present invention are in a purified state, contacting can be performed by adding test molecules (samples) to the purified preparations. If the polypeptides of the present invention are expressed in cells or cell extracts, contacting can be carried out by adding test molecules (samples) to the cell cultures or the cell extracts, respectively. If the test molecule is a protein, contacting can be carried out, for example, by introducing a vector comprising a DNA encoding the protein into cells expressing a polypeptide of the present invention, or by adding the vector to cell extracts in which a polypeptide of the present invention is expressed.

Furthermore, test molecules used for the screening methods and the polypeptides of the present invention can be appropriately labeled for use as necessary. Examples of labels include radioactive labels, fluorescent labels, and enzyme labels.

The binding activities can be measured suitably by methods well known to those skilled in the art, such as methods that utilize the yeast two-hybrid system and methods that utilize immunoprecipitation. Various methods for measuring interactions between proteins (binding activities) are known, and measurement of the binding activity of the present invention is not limited to particular methods.

For example, a polypeptide of the present invention is contacted with a sample such as a cell culture supernatant or cell extract, containing test molecules whose binding activities to the polypeptide of the present invention are to be evaluated, and then an antibody of the present invention can be added to coimmunoprecipitate the molecules and the polypeptide of the present invention. Binding between a test molecule and a polypeptide of the present invention can be determined based on whether the electrophoretic mobility of the immunoprecipitated product is different from that obtained when the polypeptide of the present invention is used alone. Furthermore, the test molecules in the sample in which binding was detected can be collected by methods that utilize the binding of the polypeptide of the present invention, such as affinity chromatography.

Furthermore, methods of the present invention can be carried out by using phage vectors to produce cDNA libraries from tissues or cells that are predicted to express test molecules, such as proteins, which may bind to the polypeptides of the present invention, expressing the libraries on agarose, then transferring the proteins onto a filter, reacting them with labeled polypeptides of the present invention and performing "West Western blotting", which detects plaques expressing the test molecules that bind to the labeled polypeptides.

In addition, techniques that can be generally used by those skilled in the art include: methods that react the polypeptides of the present invention immobilized on a solid or such with synthetic compounds, natural product banks, random phage peptide display libraries or such, and then screen for molecules that bind to these polypeptides; and methods for isolating candidate compounds by high-throughput screening using combinatorial chemistry techniques.

The test compounds are not particularly limited, and for example, various known compounds and peptides, or a group of random peptides produced by applying phage display methods may be used. "Double phage display method" (J. Castillo, B. Goodson, and J. Winter: T7 displayed peptides as targets for selecting peptide specific scFvs from M13 scFv display libraries: J. Immunol. Methods: 257:1-2:117-22: 2001), which uses phages displaying the polypeptides of the present invention and phages displaying the aforementioned group of random peptides, may also be suitable for use in the screening methods of the present invention.

Furthermore, culture supernatants of microorganisms, plants, natural components derived from marine organisms, and such can also be subjects of screening. Other examples include living tissue extracts, cell extracts, expression products of gene libraries, and such, but are not particularly limited thereto.

Polypeptides are generally gene products encoded by one of the strands of double stranded DNAs. Peptides that are postulated to have an amino acid sequence encoded by the other strand are called antisense peptides. Blalock et al. proposed a hypothesis that antisense peptides interact with the original peptides (sense peptides) in 1984, and thereafter, there have been many reports on interactions between sense peptides and antisense peptides. Therefore, molecules that bind to the polypeptides of the present invention can be efficiently obtained by subjecting antisense peptides derived from the complementary strand sequences of the DNAs encoding the polypeptides of the present invention to the screening methods of the present invention as test molecules.

Molecules that bind to the polypeptides of the present invention are useful as inhibitors of brain-localizing activity, inducers that enhance or modify brain-localizing activity, receptors (molecules that induce transmigration), and such.

The present invention also relates to methods for obtaining polypeptides having brain-localizing activity. A preferred embodiment of the present invention provides methods of screening for (methods for obtaining and isolating) polypeptides having brain-localizing activity, in which the methods comprise the following steps (a) to (d):

(a) preparing phage particles that display test polypeptides on their phage coat proteins;

(b) administering the phage particles to a non-human animal;

(c) collecting phage particles from the brain tissues of the non-human animal; and (d) selecting test polypeptides displayed on the phage particles collected in step (c) as polypeptides having brain-localizing activity.

The sequence of the test polypeptides in the above-mentioned methods is not particularly limited, and polypeptides comprising any amino acid sequence can be used. Generally, the test polypeptides of the present invention are multiple types of polypeptides comprising random amino acid sequences. Furthermore, the methods of the present invention can be performed efficiently by subjecting polypeptides that comprise an above-described amino acid motif sequence or a portion of the motif sequence, or polypeptides with the above-mentioned "Feature 1" as test polypeptides for the screening methods of the present invention.

The length of the test polypeptides is not particularly limited as long as it is an acceptable length to be displayed on phage coat proteins. Those skilled in the art can appropriately set the length of the test polypeptides according to the type of the phage and so on.

Polypeptides comprising any amino acid sequence can be easily produced by those skilled in the art using known techniques. For example, test polypeptides can be prepared using a commercially available peptide synthesizer and such.

Methods for displaying arbitrary polypeptides on phage coat proteins in step (a) are techniques generally known to those skilled in the art as "phage display methods". Libraries of molecules are usually prepared by utilizing the life cycle of phages to display arbitrary polypeptides on phage coat proteins. For example, randomized DNAs are chemically synthesized and then inserted into phage DNAs using genetic engineering techniques. By introducing these DNAs into host cells such as E. coli, phage molecules are biosynthesized, and polypeptides encoded by the randomized DNAs are displayed on viral coat proteins.

More specifically, the method (procedure) described in the Examples is an example of a step of producing phage particles displaying test polypeptides on their coat proteins.

Phages that can be used in the screening methods of the present invention are known phages such as M13, T7, fl, and fd. Examples of phage coat proteins include pIII, 10A, 10B, and capsid. Libraries that can be displayed on the pIII protein are commercially available, and these libraries can be suitably used in the screening methods of the present invention.

Furthermore, in a preferred embodiment of the present invention, phage particles that may bind to cerebrovascular endothelial cells can be selected by panning the phage particles produced in step (a), prior to step (b). This procedure allows the screening of the present invention to be performed efficiently.

The panning method is a selection method using protein interactions, and can be suitably performed by those skilled in the art according to the type of the phage and such. For example, the panning method can be used in the screening methods of the present invention as follows. First, to concentrate by culturing phages that can easily bind to cerebrovascular endothelial cells, phages that react with control cells (mouse glioma cells) and bind to them non-specifically are removed by absorption, and phages that specifically attach to mouse brain-derived vascular endothelial cells (such as MBEC4) are concentrated. More specifically, panning can be performed using the procedures described in the Examples.

In step (b), non-human animals to which the phage particles are administered include mice, rats, gerbils, cats, cattle, and monkeys. Additional examples include domestic animals and pets.

Phages that are administered in step (b) are not necessarily whole phage particles, and the screening methods of the present invention can be performed by administering to a non-human animal, for example, only the test polypeptide-displaying coat proteins.

Administration into the body of a non-human animal is generally carried out by intraarterial injection, intravenous injection, subcutaneous injection, transdermal administration, oral administration or such, and preferably by intraarterial injection.

In step (c), phage particles can be generally collected from brain tissues as follows. The brain is removed from a non-human animal, and serial dilutions of the brain homogenates are prepared. Next, the diluted solutions are spread over agar media, phage plaques are formed and picked, and then phage particles are collected. However, this method is only an example, and those skilled in the art can appropriately collect phage particles from brain tissues according to the type of the phage and such.

In addition, the amino acid sequences of the polypeptides selected in step (d) can be determined by methods known to those skilled in the art.

All prior art references cited herein are incorporated by reference.

BRIEF DESCRIPTION OF THE DRAWINGS

FIG. 3 shows the construction of a phage library (random peptides) using the T7 Select System.

FIG. 4 describes the T7 Select System.

Left (top and bottom): control group (avidin-colloidal gold): the colloidal gold label is not observed in nerve cells. (Top): hippocampal pyramidal cells (CA1 to CA2 region); (Bottom): cerebellar Purkinje cell region; Center (top and bottom): administration of biotin-conjugated T2J002+avidin (Av)-gold particles. Right (top and bottom): administration of biotin-conjugated T2J004+avidin (Av)-gold particles. Peptide conjugates allowed gold colloids to be transported into the cerebral parenchyma.

Figure 10:
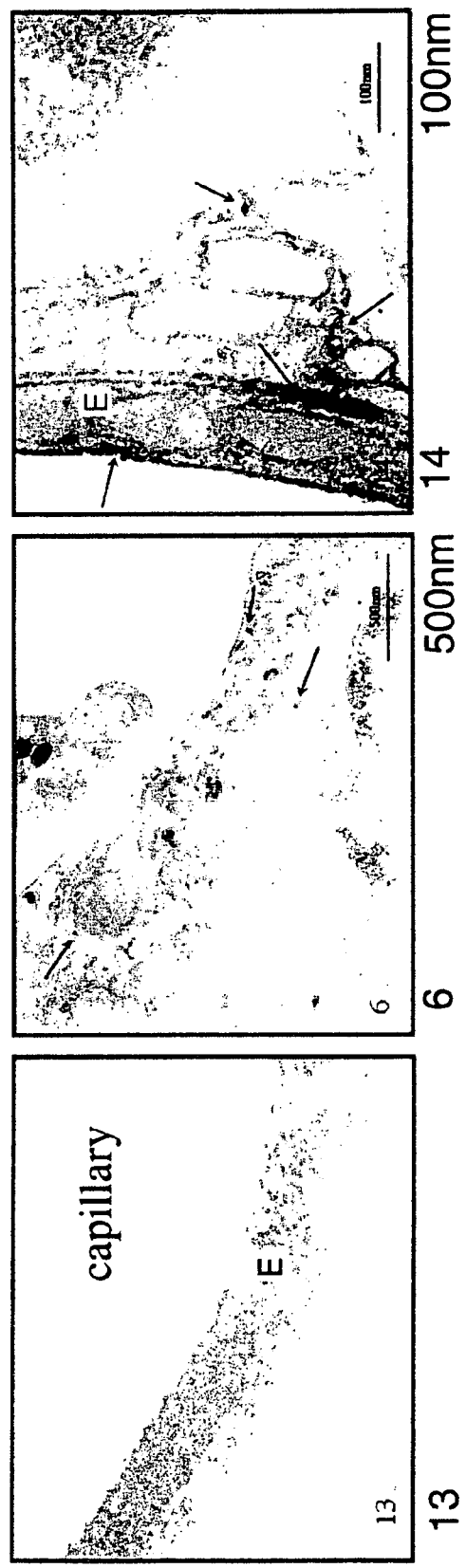

FIG. 10 is a set of electron micrographs showing the presence of conjugates with a peptide of the present invention and colloidal gold in the pyramidal cell layers CA1-CA2.

Left: control group (administration of avidin-colloidal gold only); no reaction was observed in the vascular endothelium. Center: Biotin+peptide group (1); administration of biotin-conjugated T2J002+Av-gold. Biotin+peptide group (2) shows an electron microscope (EM) image of the immunoreaction by the pre-embedding method, where observations were made by administering biotin-conjugated T2J002, preparing ultrathin sections, and then detecting with Av-gold. No reaction was observed in the vascular endothelia in the control group (left). In the experimental groups, deposition of DAB indicating an immunoreaction in the endothelial cells was observed (arrows). This reaction was observed in the endothelial cells as well as outside the blood vessels (cerebral parenchyma).

Figure 11:
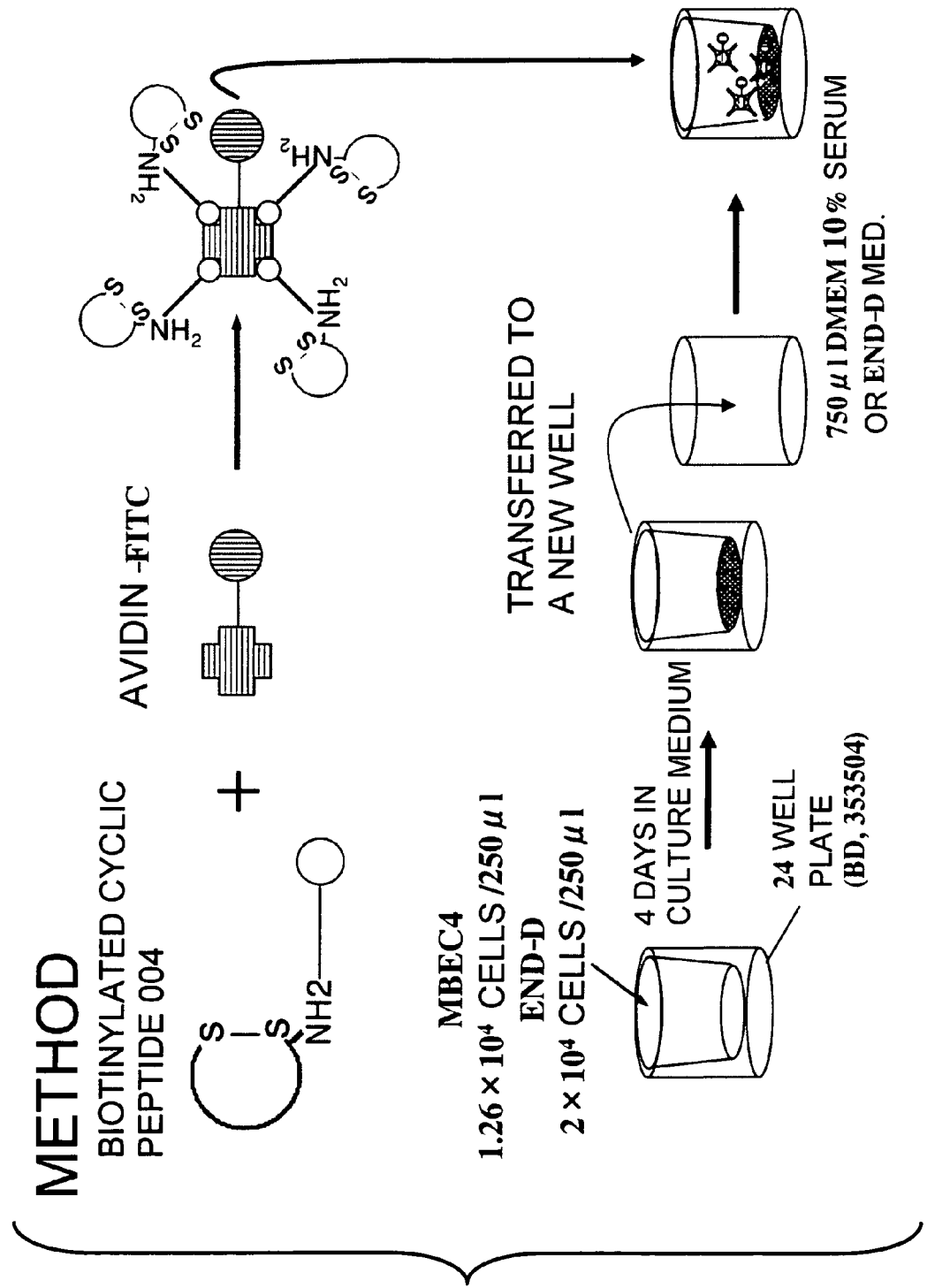

FIG. 11 schematically shows an experiment for evaluating the permeability into MBEC4 using the peptide conjugates of the present invention.

Figure 12:
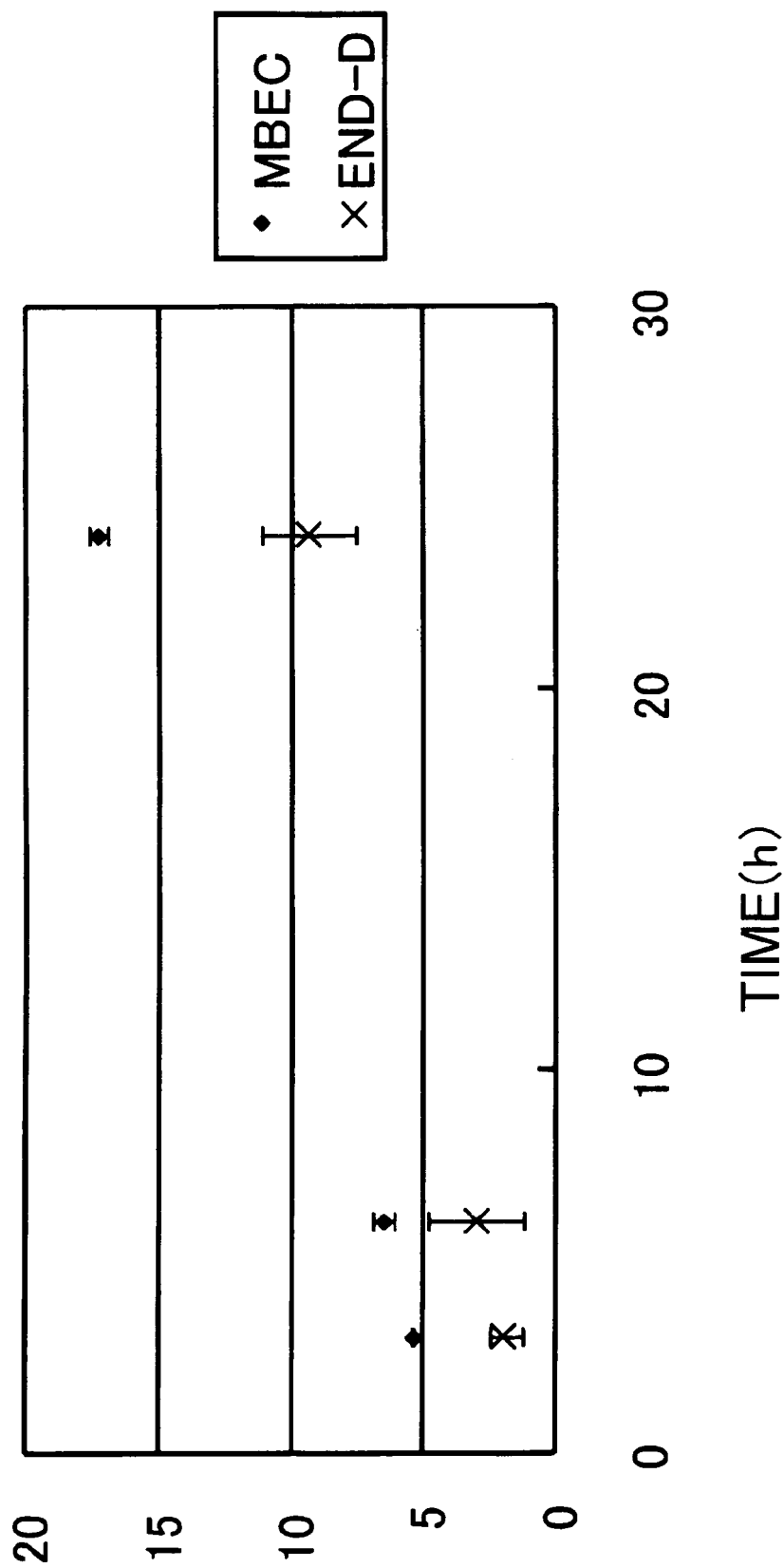

FIG. 12 shows the MBEC4 permeability of a peptide conjugate of the present invention (T2J004). Avidin-FITC 0.4 nmol/insert was attached to the peptide at 1:4 ratio and time-dependent change in the MBEC4 permeability was examined.

Figure 13:
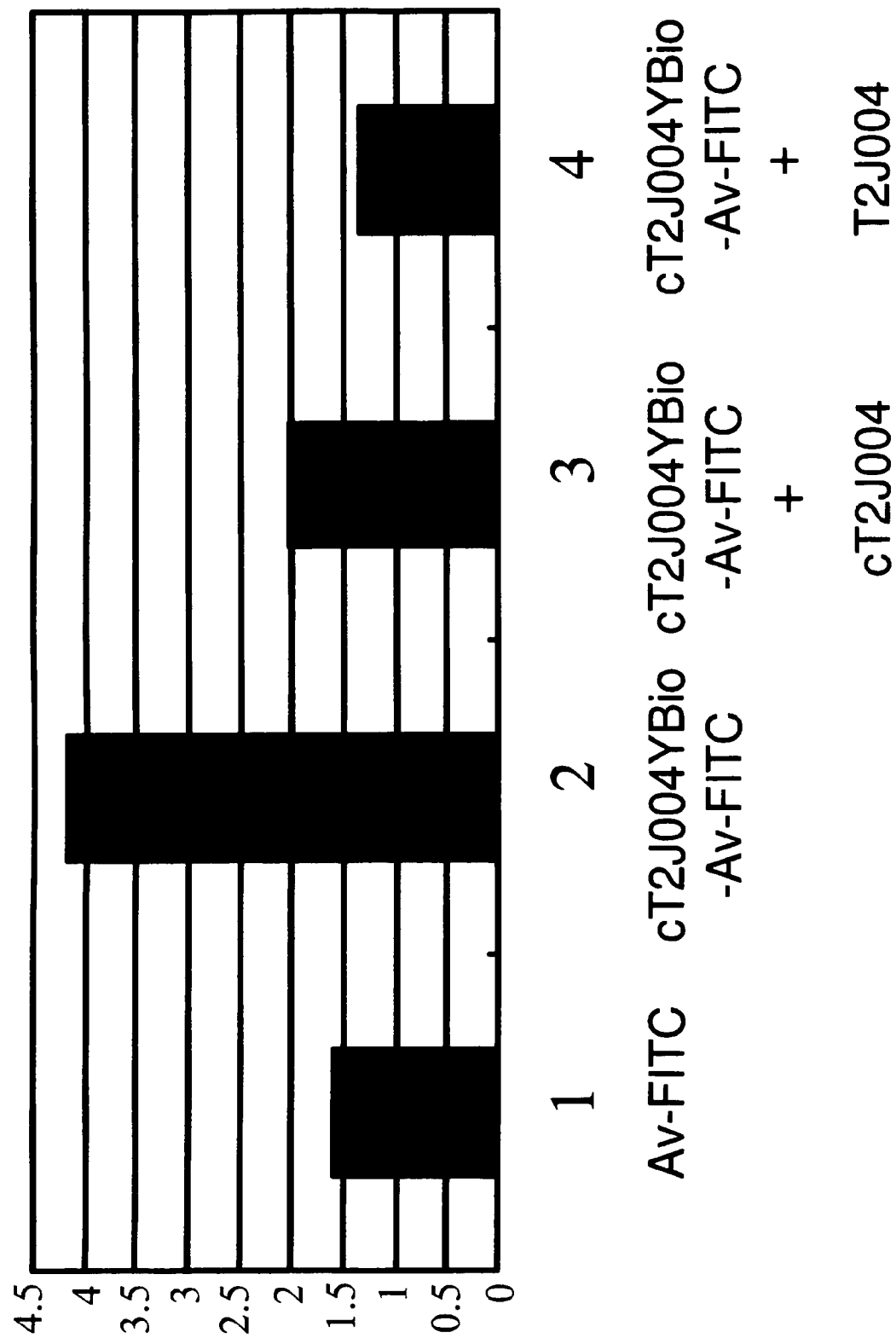

FIG. 13 shows increases in the permeability by peptide conjugates and inhibitory activity by unlabeled peptides in a blood-brain barrier model.

Addition of biotin conjugate T2J004Y+Av-FITC to a blood-brain barrier model prepared using MBEC4, as compared to the addition of Av-FITC, showed an approximately three-fold increase in permeability when the fluorescence intensity of the lower layer was measured. This effect was found to be significantly inhibited by cyclic T2J004 and linear T2J004.

Figure 14:
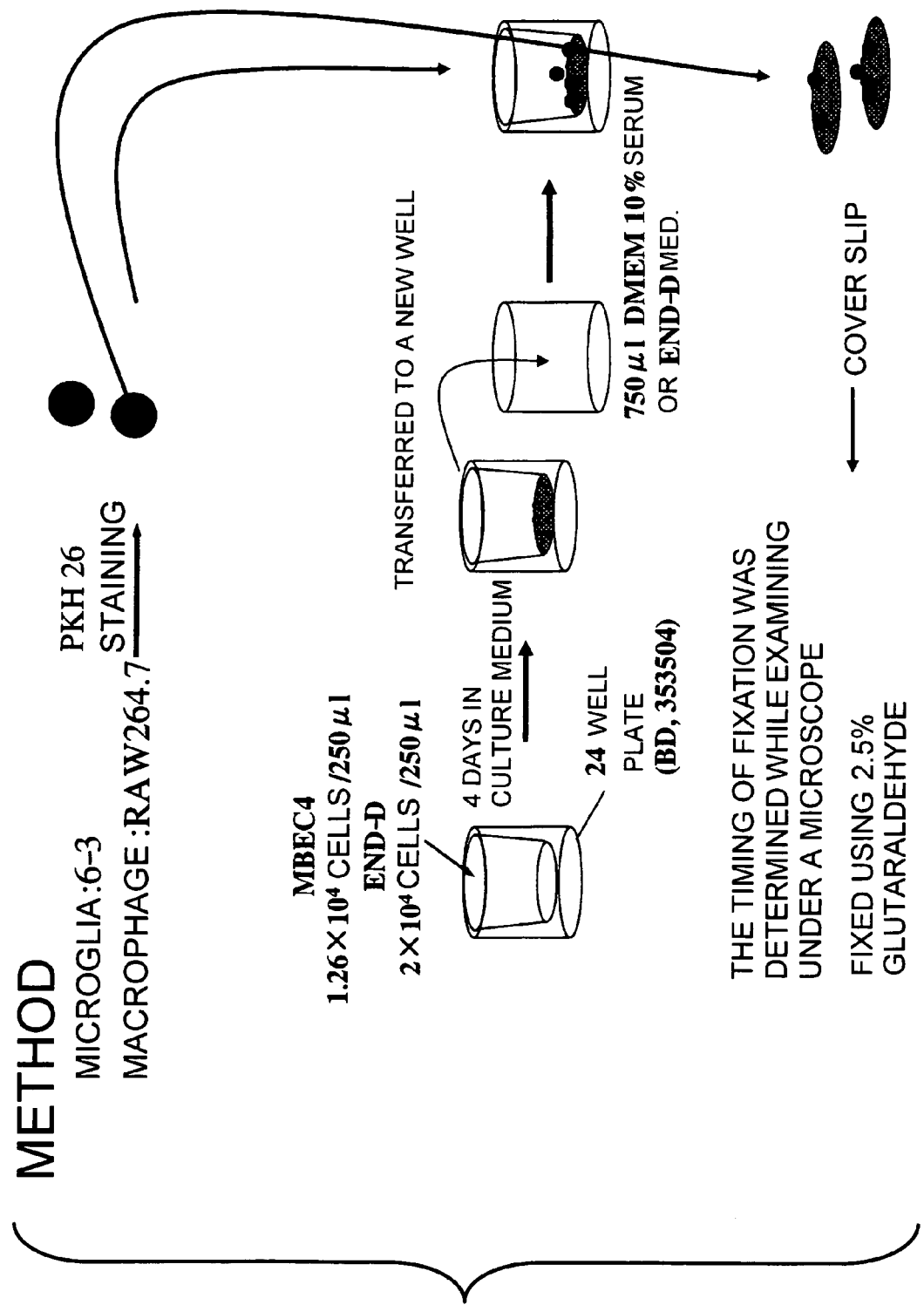

FIG. 14 schematically shows an experiment for evaluating the MBEC4 permeabilities of microglias and macrophages.

Figure 15:
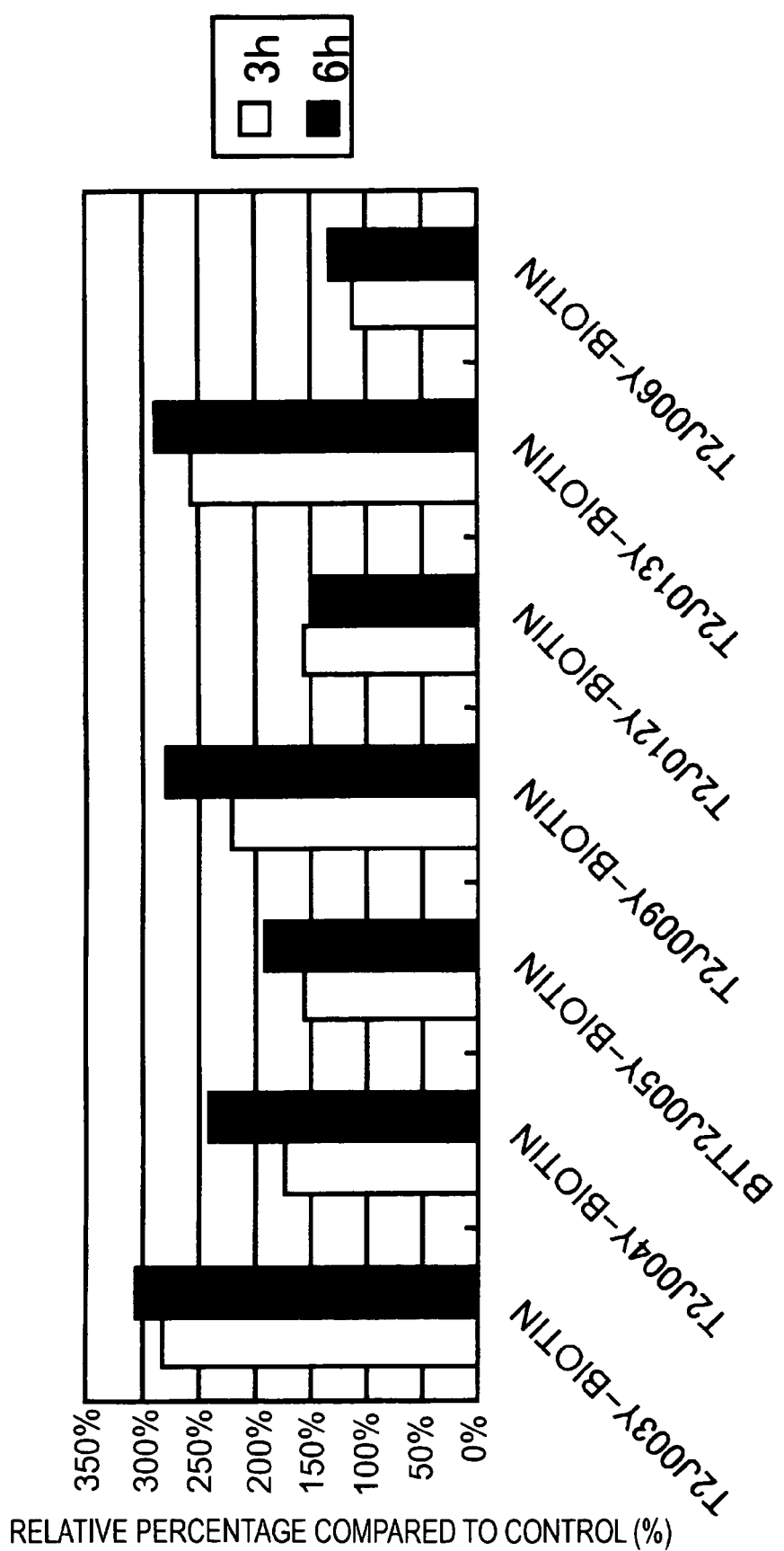

FIG. 15 shows the MBEC4 permeability of various peptide conjugates of the present invention.

Figure 16:
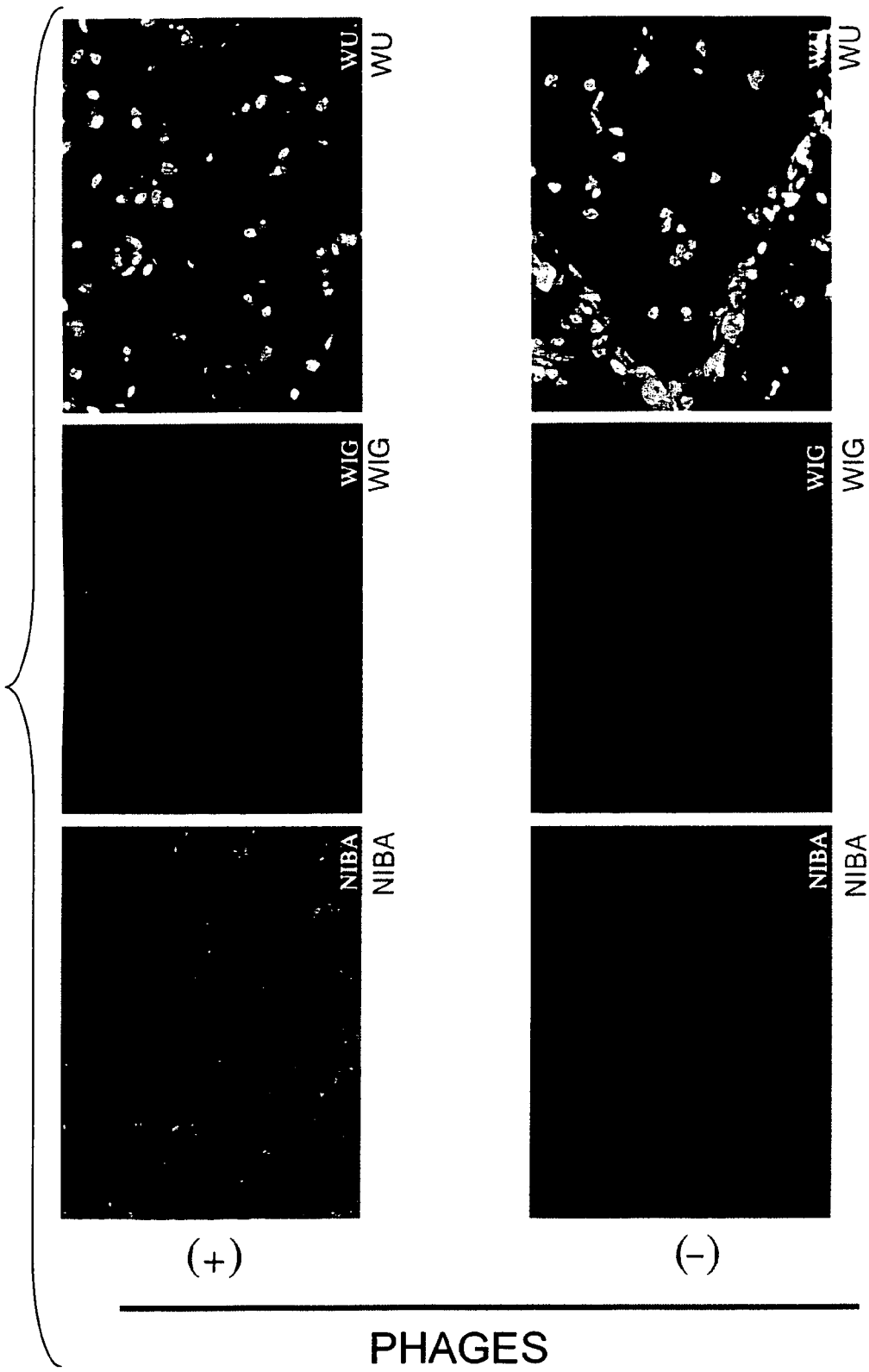

FIG. 16 is a set of photographs showing the detection of recombinant brain-localizing phages in the brain using a 4F111 anti-M13 phage antibody.

After brain-localizing phages (top row) and control phages (bottom row) were administered into blood vessels, the brains were removed 30 minutes later and stained using a 4F111 anti-M13 phage antibody. In the brain administered with the brain-localizing phages, phage particles were detected.

Left: fluorescence photographs showing specific binding using NIBA filter

Center: detection of non-specific binding using WIG filter

Right: nuclear staining using Hoechst 23384 (identification of cells)

Figure 17:
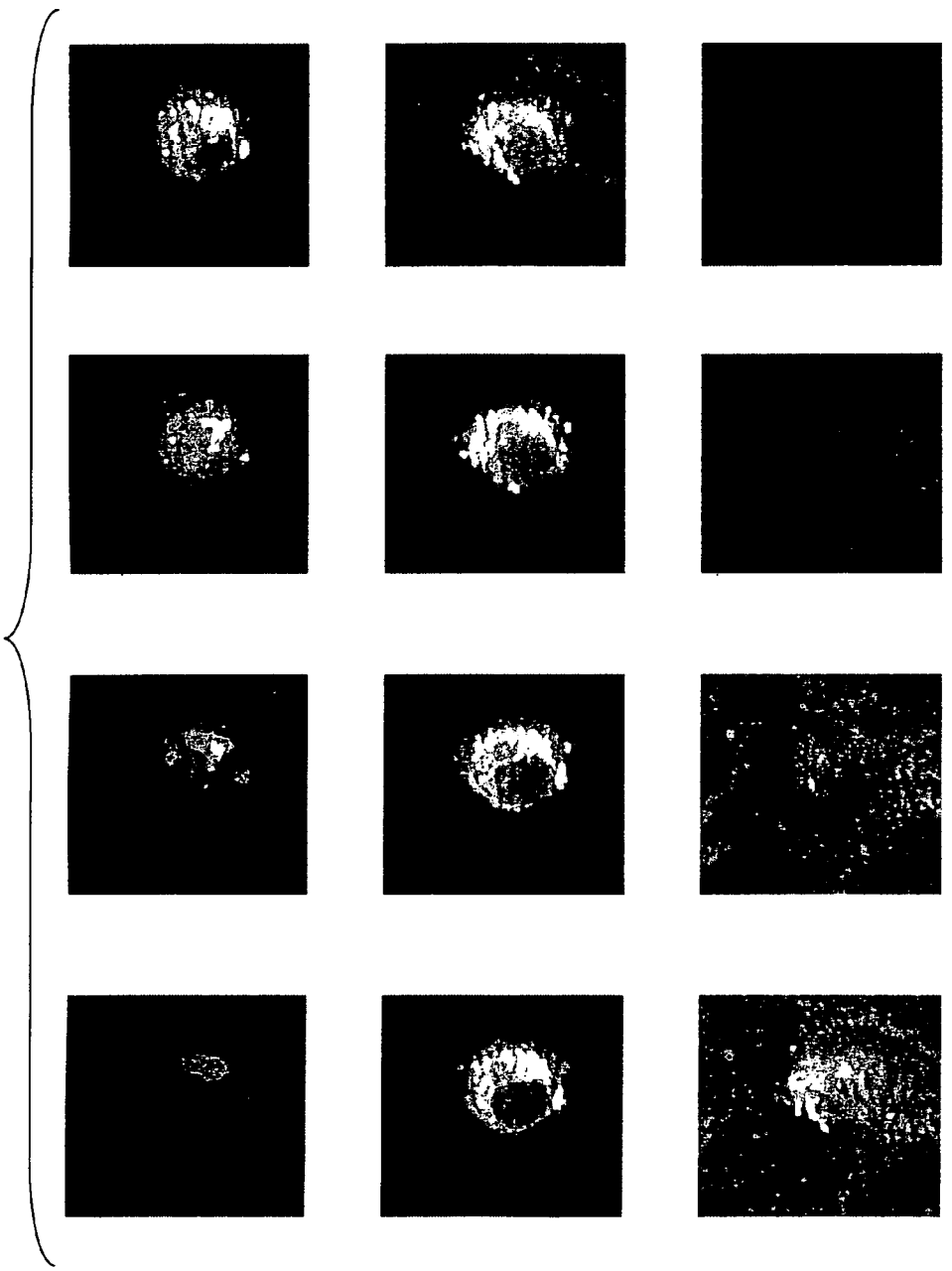

FIG. 17 is a set of photographs showing detection of the transcytosis of microglias using a confocal microscope.

In the blood brain barrier model using MBEC4, transcytosis was detected 4 hours after addition of microglias. Images of yellowish-orange microglias passing through the green vascular endothelial cells can be observed from the photographs.

Figure 18:
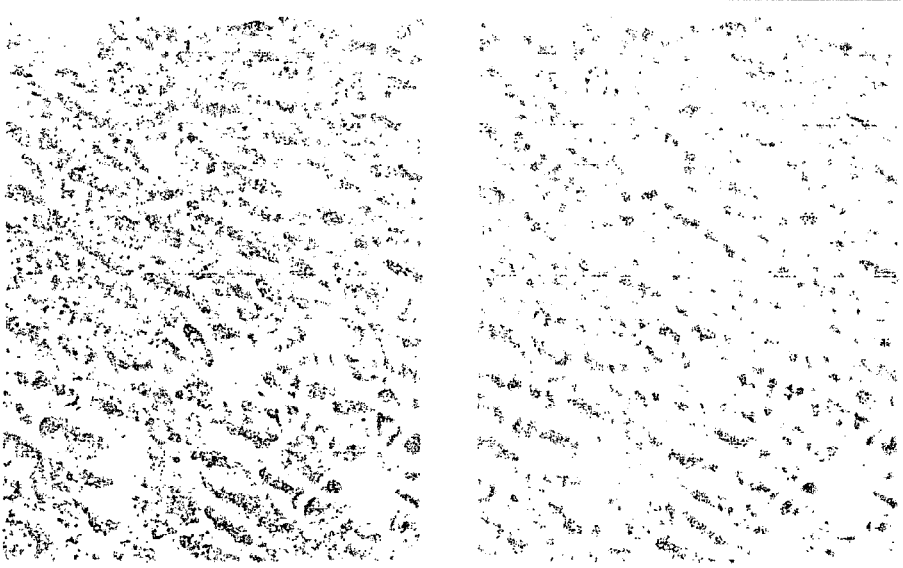

FIG. 18 is a set of photographs showing phase-contrast microscope images (left) and fluorescence microscope images (right) an hour after addition of microglias to the vascular endothelial cells.

FIG. 19 is a set of photographs showing the result of observation under a light microscope after toluidine blue staining. The vertical sections of the MBEC4 blood brain barrier model, to which microglias (left) or macrophages (right) were added, were stained with toluidine blue.

Figure 20:

FIG. 20 is an electron microscopic photograph of MBEC4. The black zone at the center is a tight junction (a barrier structure characteristically found in blood-brain barriers).

Figure 21:
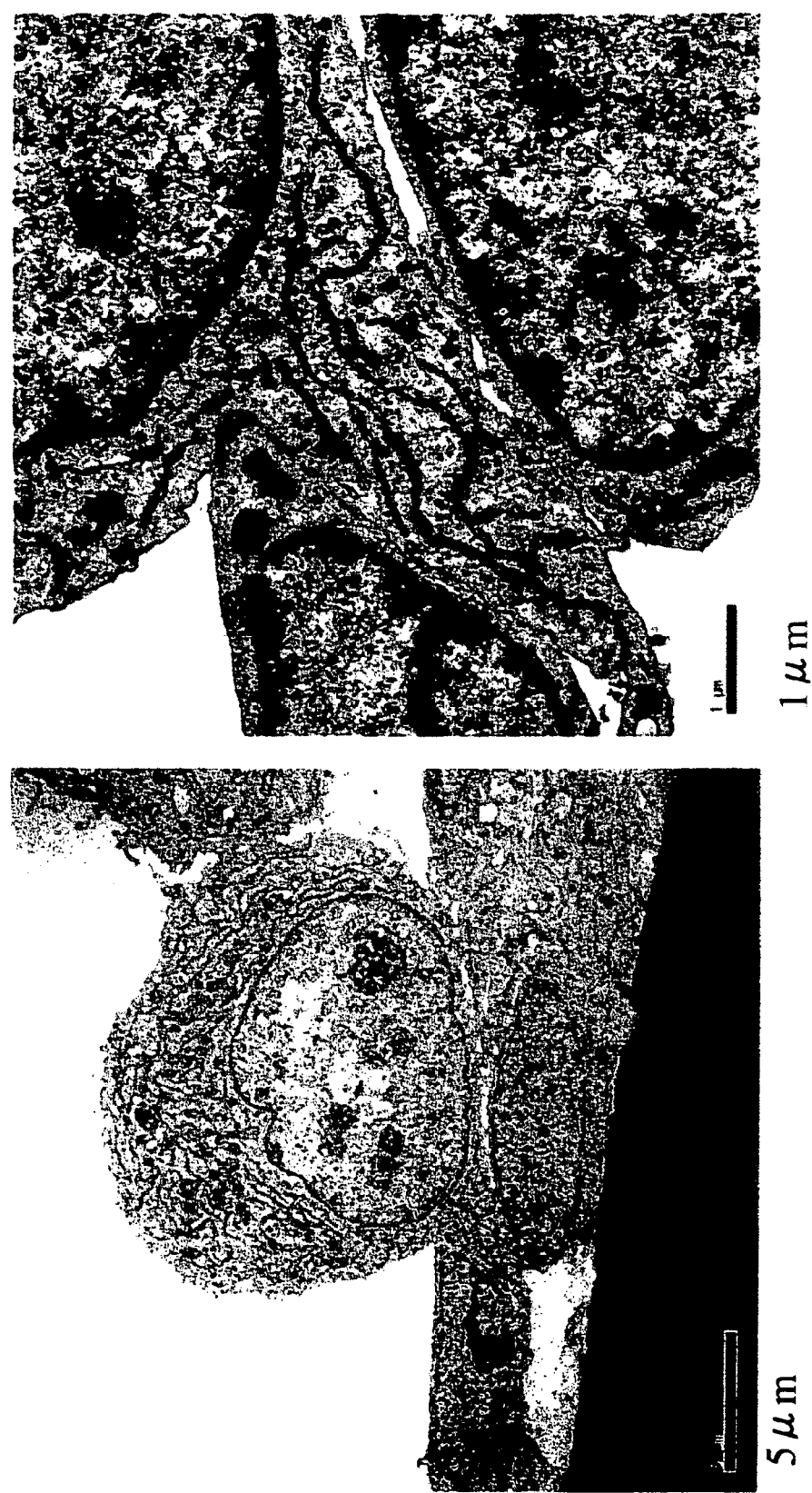

FIG. 21 shows electron microscope images depicting the passing of microglias through the blood-brain barrier model.

Figure 22:
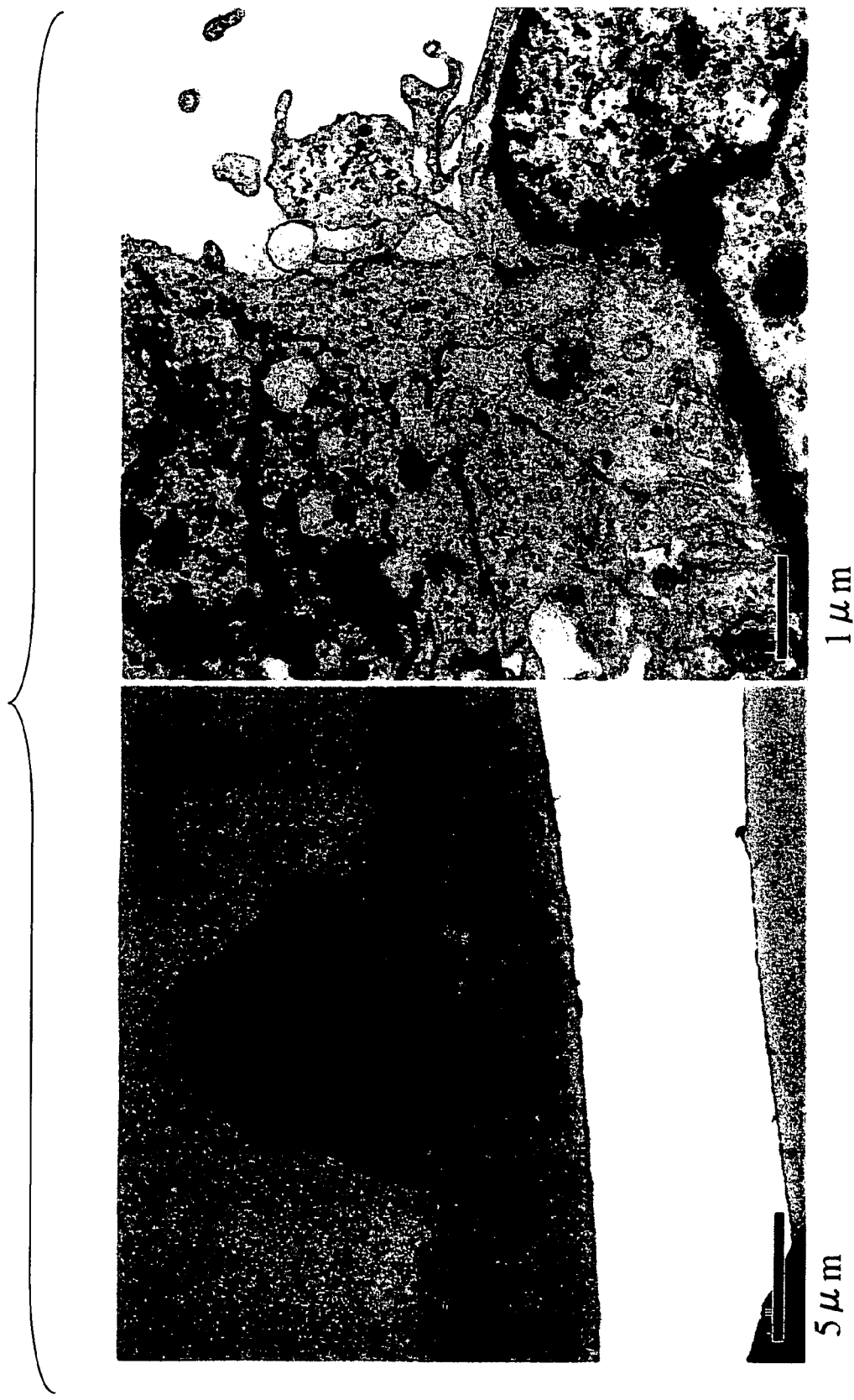

FIG. 22 shows electron microscope images depicting the passing of microglias through the blood-brain barrier model. Invagination of microglial protrusions into the MBEC4 cells forming the blood-brain barrier was clearly observed.

Figure 23:
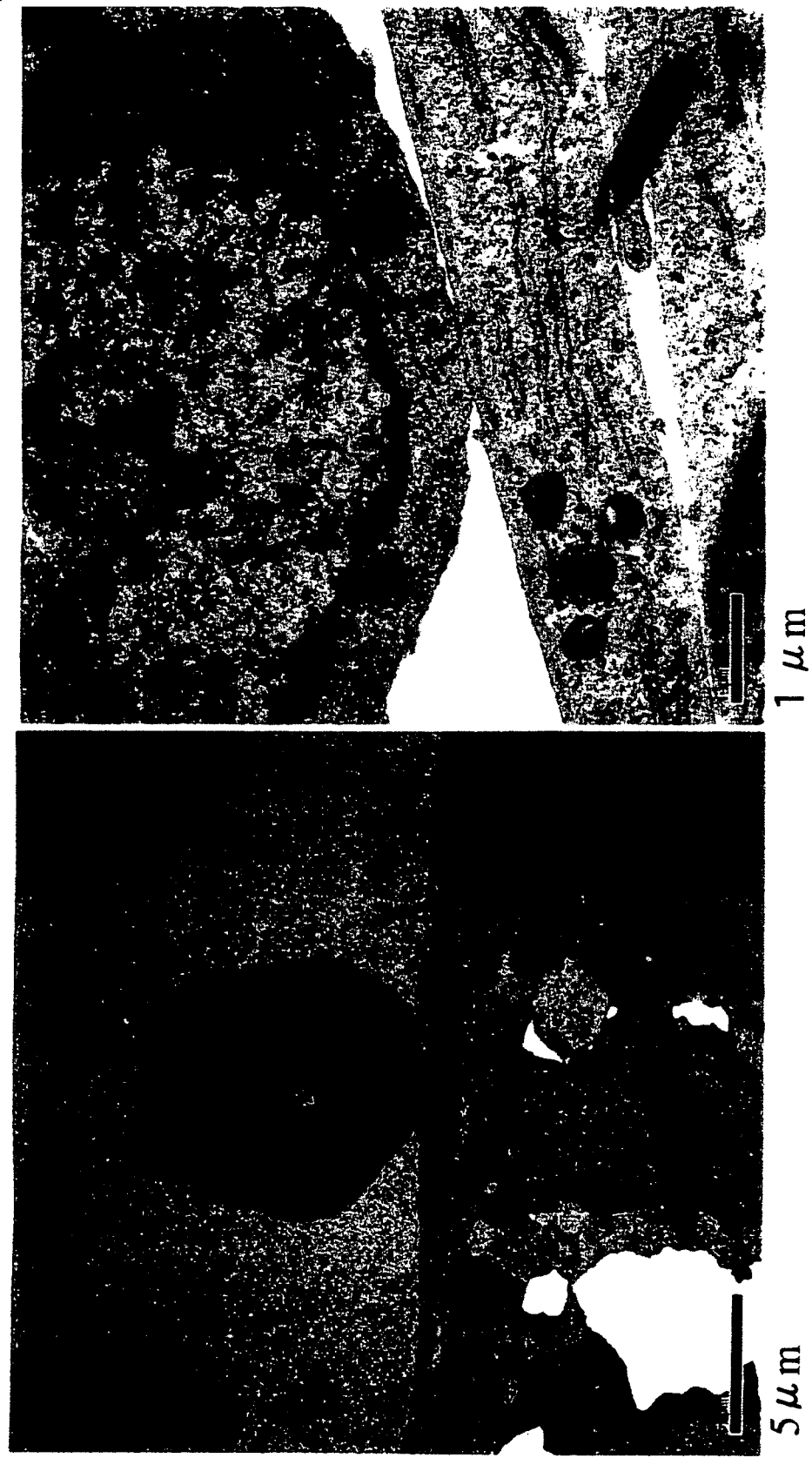

FIG. 23 shows the adhesion of macrophage cell line Raw264.7 to MBEC4. The macrophages adhered only loosely to MBEC4 that form the blood-brain barrier. Permeation into the cell layer was not observed.

Figure 24:
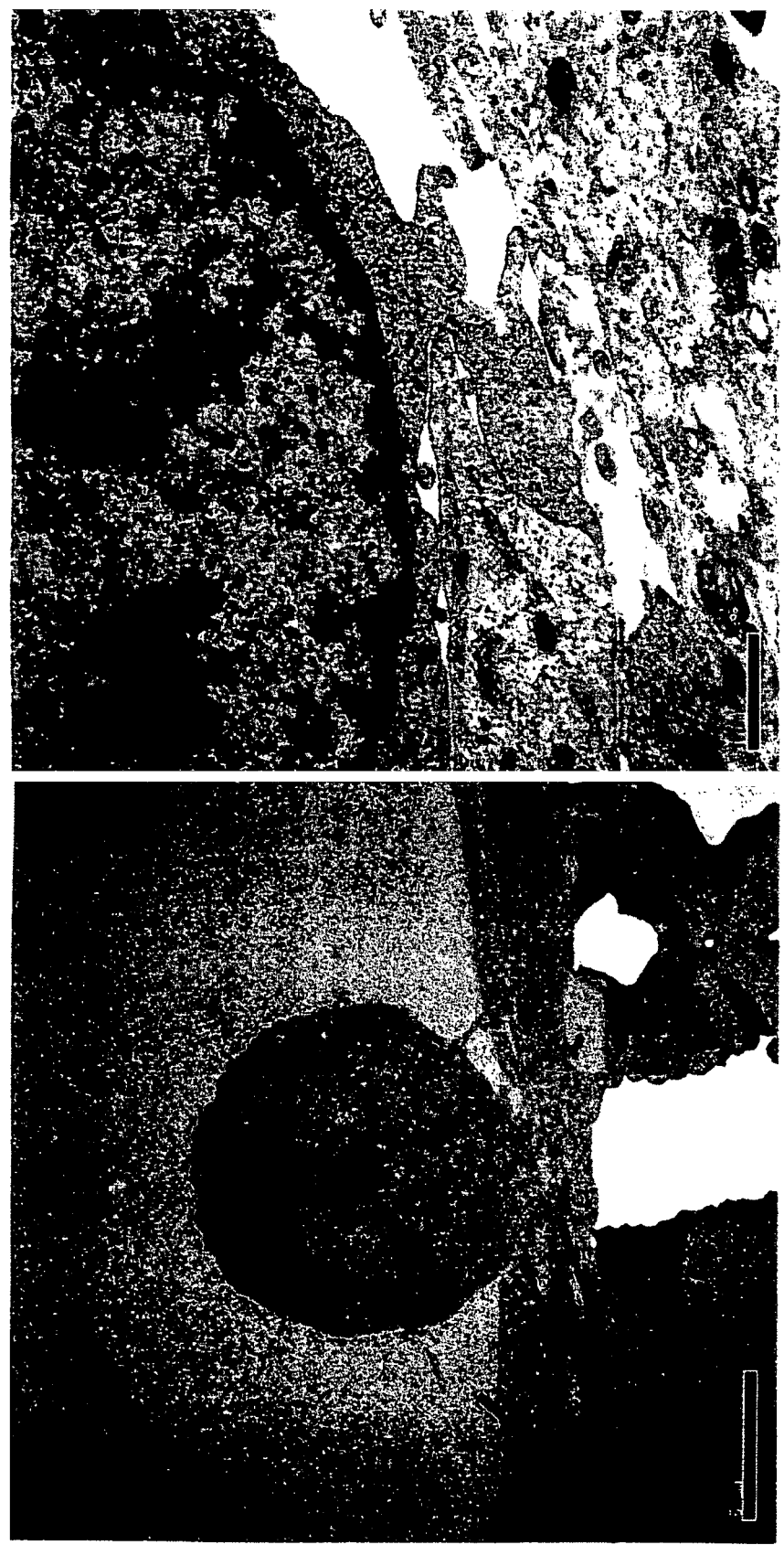

FIG. 24 shows the adhesion of macrophage cell line Raw264.7 to MBEC4. The macrophages adhered only loosely to MBEC4 that form the blood-brain barrier. Permeation into the cell layer was not observed.

BEST MODE FOR CARRYING OUT THE INVENTION

Herein below, the present invention will be specifically described using Examples, however, it is not to be construed as being limited thereto. PEG6000 was purchased from Wako, and trypsin EDTA, Luria broth base, and penicillin-streptomycin were purchased from GIBCO. Furthermore, EDTA 2Na, Agarose 36G, and T7 Select 1-1 Cloning kit were purchased from Nacalai, Funakoshi, and Novagen, respectively.

EXAMPLE 1

Cell Culture (1) Mouse 203 Glioma Cells 203 glioma cells were cultured at 37° C. under 5% $CO_2$ in MEM (SIGMA) supplemented with 10% FCS (GIBCO), 5 μg/ml insulin (SIGMA), and 0.22% glucose (Katayama). Subculturing was performed by plating $2 \times 10^5$ cells/7 ml in 10 cm plates (Falcon), and the cells were passaged every 7 days. For panning, 203 glioma cells were plated in 10 cm plates at $2 \times 10^6$ cells/7 ml and used for panning 4 days later.

(2) Mouse Vascular Endothelial END-D Cells

END-D cells were cultured at 37° C. under 5% $CO_2$ in DMEM (SIGMA) supplemented with 10% inactivated FCS, 100 unit/ml penicillin, and 100 mg/ml streptomycin. Subculturing was performed as follows. The cells were washed once with PBS (−) followed by addition of 5 ml of 0.25% trypsin/1 mM EDTA 4Na, left to stand for 3 minutes, and then detached by flushing with 5 ml of the medium. Next, the cells were precipitated by centrifugation at 1200 rpm for 5 minutes, and the pellet was washed once with the medium after the supernatant was removed. Subsequently, the cells were plated onto 10 cm plates at $3 \times 10^5$ cells/7 ml, and passaged every 3 to 4 days. END-D cells to be used for panning were plated onto collagen-coated 10 cm plates at $3 \times 10^6$ cells/7 ml, and used for panning 4 days later. Collagen-coated plates were prepared by pouring 5 μg/cm² of collagen (Nitta Gelatin, cellmatrix type I-C) into 10 cm plates, leaving them to stand for 1 hour, and then washing twice with PBS(−).

(3) Mouse Brain-Derived Vascular Endothelial Cells MBEC4

MBEC4 cells were cultured at 37° C. under 5% $CO_2$ in DMEM supplemented with 10% FCS, 5 μg/ml of heparin (SIGMA), and 30 μg/ml of Endothelial cell Growth Supplement (ECGS; Upstate Biotechnology). Subculturing was performed by plating $2 \times 10^5$ cells/7 ml onto 0.2% gelatin (Katayama)-coated 10 cm plates, and the cells were passaged every 3 to 4 days. MBEC4 cells to be used for panning were plated onto collagen-coated 10 cm plates at $2 \times 10^6$ cells/7 ml, and used for panning 4 days later.

EXAMPLE 2

M13 Phage Display Library

1. Culturing of *E. coli* ER2738

Host *E. coli* ER2738 cells included in the Ph.D.-C7C™ Phage Display Peptide Library Kit (New England Biolabs, E8120S) were cultured overnight at 37° C. with shaking in LB medium containing 20 μg/ml of tetracycline (Katayama), and then the culture was streaked on LB plates containing 20 μg/ml of tetracycline and used as working stocks of ER2738. Fresh working stocks were produced every 2 weeks.

ER2738 used for phage amplification and titer measurements were obtained by picking single colonies from the streaked working stocks, and culturing the cells overnight at 37° C. with shaking in LB medium containing 20 μg/ml of tetracycline.

2. In Vitro Panning 2-1. Cell Fixation 10 cm plates, on which a sheet of 203 glioma cells (used as control), END-D cells, or MBEC4 cells to be used for panning was formed, were fixed on the day of use as described below. Cells of each type were fixed by removing the medium, washing once with 5 ml PBS(−), adding 3 ml of 4% PFA (Katayama)/PBS(−), letting this stand for 10 minutes, and then washing 3 times with 5 ml PBS(−). Next, blocking was performed by adding 5 ml of 2% BSA (SIGMA)/PBS(−) to the cells at 4° C. and letting them stand for 1 hour. Cells of each type were washed 6 times with 3 ml of 0.1% Tween 20/PBS(−) before the phage solution was added.

2-2. First Panning

In the first panning, $10^{11}$ pfu of M13-C7C phage library (10 μL) was dissolved in 2 ml of PBS(−), the whole volume was added to 203 glioma cells and gently shaken at room temperature for 10 minutes for adsorption. Next, the supernatant was added to END-D cells and gently shaken at room temperature for 10 minutes for adsorption. Next, the supernatant was added to MBEC4 cells and gently shaken at room temperature for 10 minutes for adsorption. After the 10-minute adsorption treatment, elution was carried out by washing the cells of each type 10 times with 5 ml of 0.1% Tween 20/PBS(−), adding 2 ml of 0.2 M glycine (Wako)-HCl (pH2.2) containing 1 mg/ml of BSA, and gentle shaking at room temperature. Immediately after collecting the eluate, the cells were rinsed using 2 ml of 0.2 M glycine-HCl (pH2.2), combined with the eluate, and neutralized by adding 1.6 ml of 1 M Tris-HCl (pH9.1). Tris was purchased from Boehringer.

Titers of each phage eluate obtained from each type of cells at each step were determined by the method indicated below in "2-2-1. Phage titration".

The phage solution eluted from the MBEC4 cells were amplified by the method indicated below in "2-2-2. Phage amplification and purification" and used for the second panning.

2-2-1. Phage Titration

Titers of the phage solutions were measured as follows.

250 μL of the overnight ER2738 culture and 3 μL of IPTG (Katayama)/ X-gal (Nacalai) mixture (50 μg/ml IPTG; 40 μg/ml X-gal) were added to a 14-ml snap cap tube (Falcon), and 2.5 ml of dissolved Top Agarose (6 μg/ml Agarose in LB medium) was added to this and mixed. The mixture was immediately spread on LB/IPTG/ X-gal plates to produce ER2378 round plates. A series of dilutions of the phage solution was prepared in TBS for titration. 10 μL of each dilution was blotted onto an ER2378 round plate, dried until the solution was no longer flowing, and cultured overnight at 37° C. The titer of the phage solution was calculated by counting the blue colored plaques.

2-2-2. Phage Amplification and Purification

The phage solution to be amplified was added to LB medium containing 20 μg/ml of tetracycline and a 1/100 volume of the overnight ER2738 culture, and then cultured at 37° C. for 4.5 to 5 hours with shaking in a conical flask with baffles. Next, this culture was centrifuged at 10,000 rpm for 10 minutes at 4° C., and the supernatant was collected. The supernatant was centrifuged at 10,000 rpm for 10 minutes at 4° C. to completely remove the ER2738 cells. One sixth volume of 30% PEG/3M NaCl (SIGMA) was added to the supernatant, and the phages were precipitated on ice overnight. After centrifugation at 10,000 rpm for 45 minutes at 4° C., the supernatant was removed by decantation and the precipitate was further centrifuged at 10,000 rpm for 10 minutes at 4° C. to collect phage pellets. The phage pellets were completely dissolved in 2 ml of TBS/0.02% NaN$_3$ (SIGMA), centrifuged at 10,000 rpm for 5 minutes at 4° C., and the supernatant was collected. CsCl (Wako) was added to the supernatant at a concentration of 0.467 g/ml, and density gradient centrifugation was performed at 80,000 rpm for 18 hours at 15° C., and then a band representing the purified phages was collected. The purified phages collected were dialyzed against TBS to remove CsCl, and stored at 4° C. after addition of 0.02% NaN$_3$.

2-3. Second Panning

In the second panning, $10^{10}$ pfu of a M13-C7C phage mixture solution was dissolved in 2 ml of PBS(−), and the whole volume was added to 203 glioma cells. This was then gently shaken at room temperature for 10 minutes to be adsorbed. Next, the supernatant was added to END-D cells, and gently shaken at room temperature for 10 minutes to be adsorbed. Subsequently, the supernatant was added to MBEC4 cells and gently shaken at room temperature for 10 minutes to be adsorbed. After the 10-minute adsorption treatment, elution was carried out by washing the cells of each type 10 times with 5 ml of 0.3% Tween 20/PBS(−), and then adding 2 ml of 0.2 M glycine-HCl (pH2.2) containing 1 mg/ml of BSA and gentle shaking at room temperature. Immediately after collecting the eluate, the cells were rinsed using 2 ml of 0.2 M glycine-HCl (pH2.2), combined with the eluate, and neutralized by adding 1.6 ml of 1 M Tris-HCl (pH9.1).

Titers of each phage eluate from each type of cells at each step were obtained by the method indicated above in "2-2-1. Phage titration".

The phage solution eluted from the MBEC4 cells was amplified by the method indicated above in "2-2-2. Phage amplification and purification" and used for in vivo panning.

3. In Vivo Panning 3-1. Phage Injection

Eight-week old male C57BL mice were used for in vivo panning. $10^{11}$ pfu/300 μL PBS of the purified phage was administered in a single application to the left carotid artery of the mice under ether anesthesia. One minute later, a tuberculin syringe (26G) coated with 15 mg/ml of EDTA was used to draw blood from the hearts, and perfusion was carried out immediately with 400 ml of 0.2 g/ml EDTA/PBS. When perfusion was completed, the cardiac perfusates were collected. After perfusion, the brains were removed, and a portion of each was sampled for titration and tissue section preparation. The left brains were used for titration, and the right brains were used for section preparation.

3-2. Tissue Sample Preparation

The tissues for titration were weighed and homogenized on ice after a double volume of the homogenization solution (20 mM HEPES (SIGMA)/0.25M sucrose/1 mM EDTA supplemented with 10 μg/ml aprotinin (Wako), 5 μg/ml leupeptin (SIGMA), and 1 mM PMSF (Wako) immediately before use) was added. Next, a volume of 100 mM LiCl (Katayama)/PBS equivalent to the amount of the added homogenization solution was added and mixed.

The blood was centrifuged at 15,000 rpm for 10 minutes at 4° C. and collected as plasma, and the titer measured.

Phage titers of the homogenates, plasma, and perfusates of the tissues were determined by the method described above in "2-2-1. Phage titration".

All of the brain homogenates were amplified and purified by the method indicated above in "2-2-2. Phage amplification and purification", and used for the following in vivo panning.

4. Phage Cloning and Sequencing 4-1. Cloning

Phage cloning was performed on brain homogenates that had undergone two rounds of in vitro panning and one round of in vivo panning, or on brain homogenates that had undergone three rounds of in vivo panning.

A series of dilutions of brain homogenates were prepared using TBS, phage plaques were formed according to the method described above in "2-2-1. Phage titration", and single plaques were picked and each placed in 1 ml of TBS. This operation was performed again to clone the phages.

4-2. Sequencing 1 ml of LB medium, 10 μL of the overnight ER2738 culture, and 100 μL of the phage clone solution were placed in a 14-ml snap cap tube, and cultured at 37° C. for 4.5 hours with shaking.

The ER2738 cells were precipitated by centrifugation at 5,000 rpm for 5 minutes at 4° C. The supernatant was transferred to a 1.5-ml Eppendorf tube and centrifuged at 10,000 rpm for 1 minute at 4° C., and the supernatant was transferred to a new 1.5-ml Eppendorf tube. Next, 400 μL of 30% PEG/3 M NaCl was added, and after mixing by inversion, left to stand overnight at 4° C.

After centrifugation at 13,000 rpm for 30 minutes at 4° C., the supernatant was removed by decantation, the residue was further centrifuged at 13,000 rpm for 30 minutes at 4° C., and the remaining supernatant was completely removed by aspiration.

100 μL of iodide buffer (4 M NaI (SIGMA)/1 mM EDTA/ 10 mM Tris pH8.0) was added to the precipitated phage and suspended to completely dissolve the phage. Next, 250 μL of ethanol was added and mixed by inversion. After incubation at room temperature for 10 minutes, this was centrifuged at 15,000 rpm for 10 minutes at room temperature, and the supernatant was removed. The precipitate was washed gently with 1 ml of 70% ethanol and centrifuged at 15,000 rpm for 5 minutes at room temperature. The supernatant was removed by decantation, and the precipitate was dried in a desiccator for 5 minutes. This precipitate was dissolved in 30 μL of TE and was used as a sequence template. Sequencing was performed on Gene Rapid SEQ 4×4 (Amersham), using −28 gIII sequencing primer (5'-GTA TGG GAT AAA CAA C-3'/SEQ ID NO: 13) that comes with Ph.D.-C7C™, and Thermo Sequence Cy5.5 Dye Terminator kit (Amersham).

5. Evaluation of Phage Clones

The obtained phage clones were amplified and purified according to the methods described above in "2-2-2. Phage amplification and purification". Ability of the purified phage clones to translocate into the brain was evaluated using titers determined according to the methods described above in "3. In vivo panning" with changing the phage dose to $10^{10}$ pfu/ 300 μL. M13-KE (New England Biolabs, E8101S; clone number 1148) was used as a control phage.

EXAMPLE 3

T7 Phage Display Library

1. Construction of T7 Phage Display Library

Oligonucleotides comprising a random sequence with EcoRI and Hind III restriction enzyme sites added to both ends, and with 81-bp (415-15: GAATCCATGCAGAATTTC (XXK)$^{15}$AAGCCTGCTACAGACCAT/SEQ ID NO: 14) or 86-bp (415-C15C: GATCCATGCAGAATTCCTGC(XXK)

Figure 1:
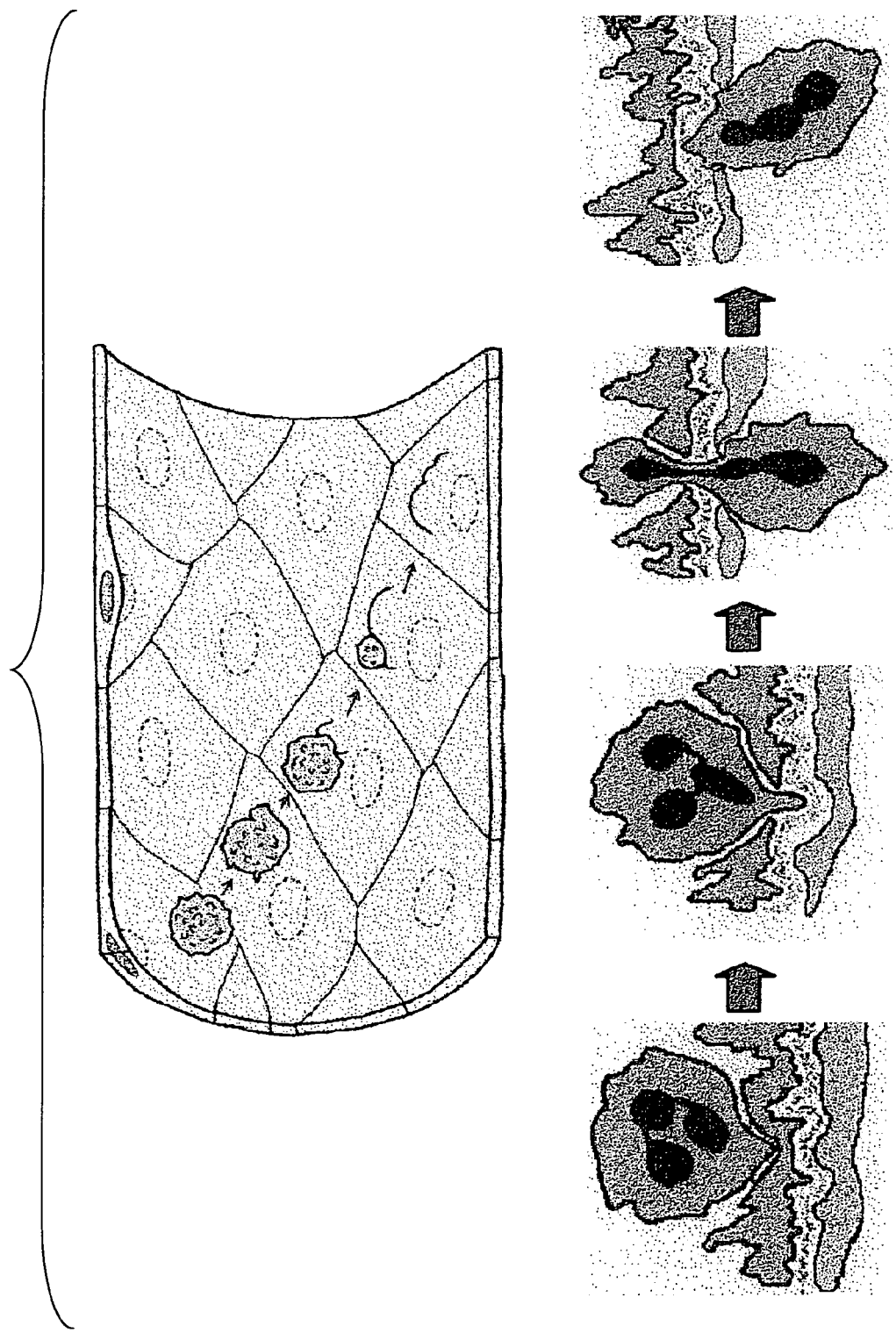
FIG. 1 shows a schematic mechanism of trans-endothelial cell migration.
Figure 2:
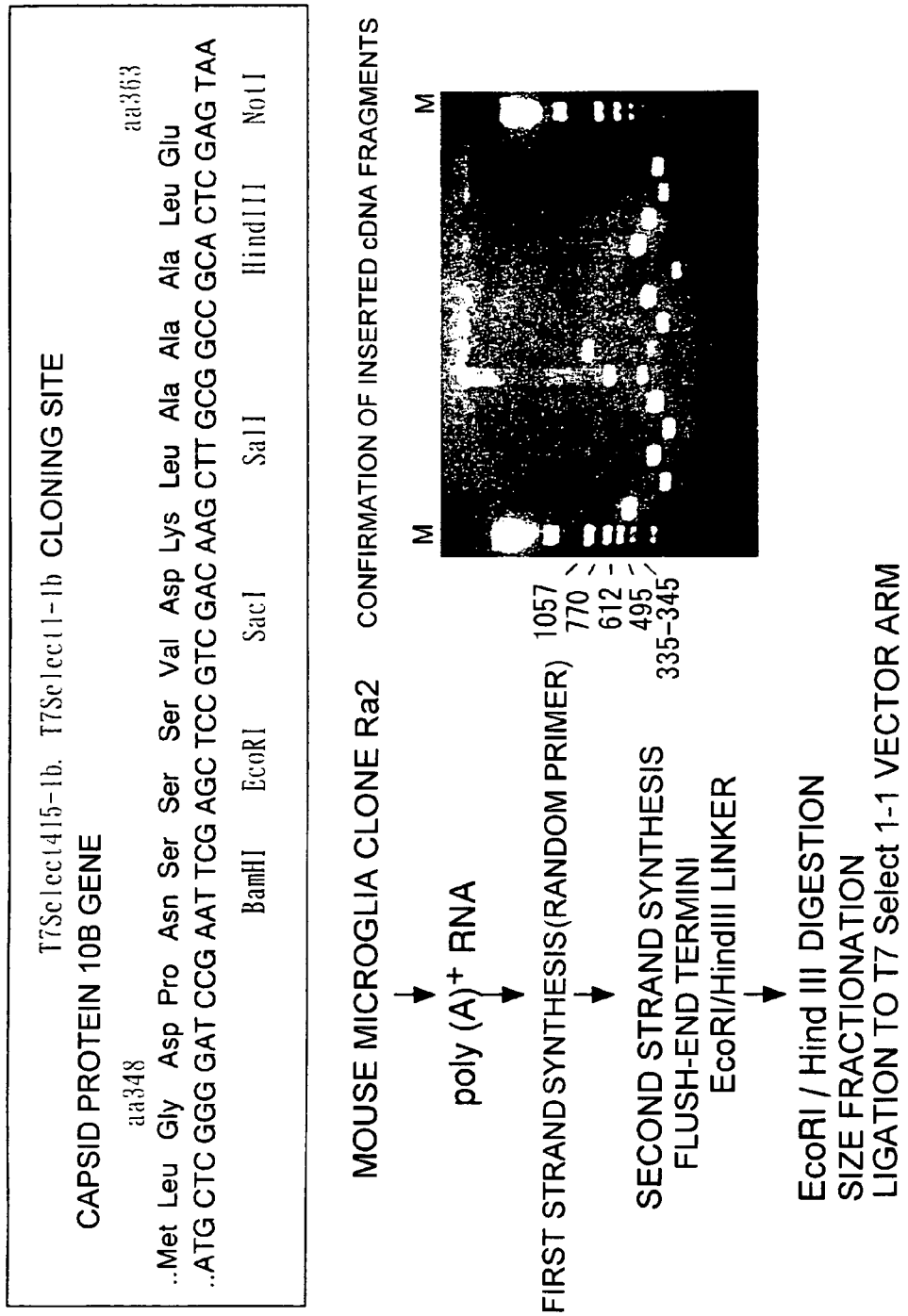
FIG. 2 is a diagram and a photograph showing the construction of a phage library using the T7 Select System. The photograph shows cDNA fragments separated on an agarose gel. In the absence of inserts, fragments of approximately 120 bp are amplified. Here, inserts of 200 bp to nearly 1 kb, which correspond to 70 to 300 amino acids, were confirmed.

¹⁵TGCAAGCTTGCTACAGACCAT/SEQ ID NO: 15), were designed and synthesized such that they would be incorporated into the T7 phage 10B gene sequence. Approximately 1.3 µg (50 pmol) of the oligonucleotide was used as a template, and PCR was performed using approximately 1.9 µg (300 pmol) of 5' and 3'-side primers to produce inserts, which comprise random sequences, for incorporation into a T7 phage display library. The produced inserts were digested with EcoRI and HindIII restriction enzymes, separated on an agarose gel, purified, incorporated between the EcoRI and Hind III sites of the pQE-TriSystem vector, and amplified using *E. coli*. The random sequences were then confirmed. After confirmation, plasmids carrying the random sequences were purified from *E. coli*, and digested with EcoRI and HindIII. The fragments of interest were separated on an agarose gel, purified, and incorporated into the T7 phage 10B gene sequence, which had been similarly digested with EcoRI and HindIII (FIGS. 2 and 3). Incorporation into the 10B gene sequence and in vitro packaging into phages were performed according to the instructions attached to the T7 Select Cloning kit (Novagen). The above-mentioned primer sequences are shown as follows:

```
415-15 5'-side primer
GAATCCATGCAGAATTCC          (SEQ ID NO: 16)

415-15 3'-side primer
ATGGTCTGTAGCAAGCTT          (SEQ ID NO: 17)

415-C15C 5'-side primer
GATCCATGCAGAATTCCTGC        (SEQ ID NO: 18)

415-C15C 3'-side primer
ATGGTCTGTAGCAAGCTTGCA       (SEQ ID NO: 19)
```

2. Culturing of *E. coli* BL21 and BLT5403

Host *E. coli* BL21 or BLT5403 cells enclosed in the T7 Select 415-1 Cloning kit (Novagen, 70015-3) were cultured overnight at 37° C. in LB medium with shaking and streaked on LB plates to produce BL21 or BLT5403 working stocks. Fresh working stocks were produced every 2 weeks. BL21 and BLT5403 cells used for phage amplification and titration were obtained by picking single colonies from the working stocks and culturing them overnight at 37° C. in LB medium with shaking.

3. In Vitro Panning 3-1. Cell Fixation

Three 10-cm plates on which a sheet of 203 glioma cells to be used for panning (as a control) had been formed and one plate prepared with MBEC4 cells were fixed on the day of use as follows. Cells of each type were fixed by removing the medium, washing once with 5 ml PBS(−), adding 3 ml of 4% PFA/PBS(−) and letting this stand for 10 minutes, and then washing 3 times with 5 ml PBS(−). Next, the cells were blocked by adding 5 ml of 2% BSA/PBS (−) and left to stand at 4° C. for 30 minutes. The blocking solution was removed immediately before phage addition by aspiration.

3-2. Panning

Figure 5:
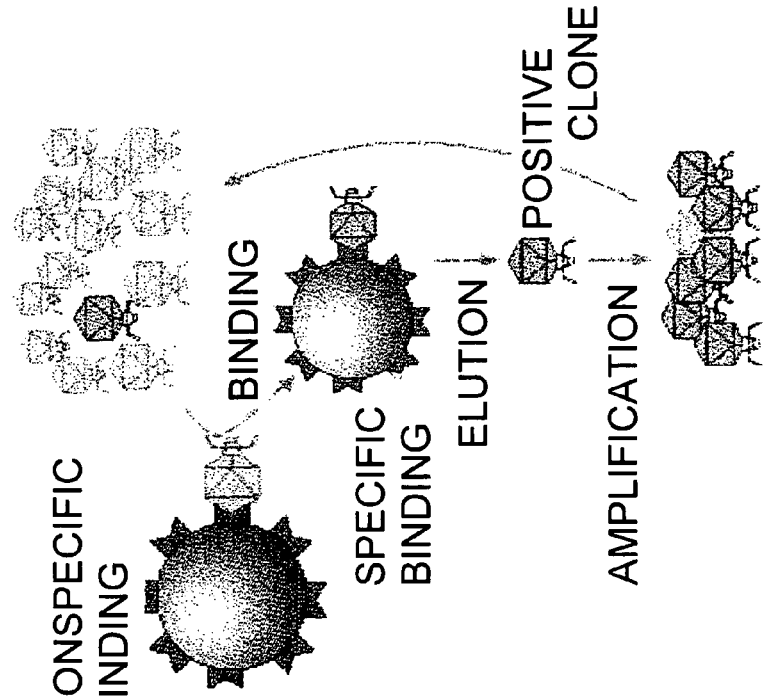
FIG. 5 describes the panning method.

A T7 Select 415-1 Cloning kit (Novagen) was used to prepare a library in which inserts were incorporated so that 15-residue random peptides placed between two cysteines were displayed, and this was used as a T7 Select 415-c15c library (FIG. 4). In in vitro panning, 2×10⁹ pfu of the T7 Select 415-c15c library was dissolved in 2 ml of PBS(−) and spread on a 4-cm plate; the total solution was collected and then spread on a new 4-cm plate. Next, 1.1 ml from the collected total solution was transferred to a new tube, 1.1 ml of 2% skim milk/PBS(−) was added thereto, and this was gently mixed at room temperature for 10 minutes. The mixture was centrifuged at 10,000 rpm for 10 minutes at 4° C., 2 ml of the obtained supernatant was added to the first 203 glioma cell plate that had been fixed and blocked by the method indicated above in "3-1. Cell fixation", and for adsorption, this was shaken gently at room temperature for 20 minutes. Next, the second and third 203 glioma cell plates were similarly treated with the supernatant. The supernatant was also added to MBEC4 cells, and shaken gently at room temperature for 30 minutes to be adsorbed. The supernatant was removed by aspiration, and washing was carried out 3 times with 10 ml of PBS(−). This was followed by washing 3 times in 2 ml of 0.01% NP-40/PBS(−) with 10 minutes of gentle shaking. Next, loosely bound phages were removed by washing with 0.1% NP-40/PBS(−) and gentle shaking for 10 minutes in 0.4 ml of 0.1% SDS/SM buffer. After rinsing with 0.6 ml of SM buffer, elution was performed by 10 minutes of gentle shaking in 0.4 ml of 0.5% SDS/SM buffer, and this was combined with the 0.6 ml SM buffer rinse solution to prepare a low-affinity phage eluate. Next, elution was performed by 10 minutes of gentle shaking in 1% SDS/SM buffer, and this was combined with the 0.6 ml SM buffer rinse solution to prepare a high-affinity phage eluate. The panning procedure is outlined in FIG. 5.

Titers of each phage eluate at each step were determined by the method indicated below in "3-2-1. Phage titration". In the titration, the titers were calculated based on phage solutions that are diluted 100 fold or more.

Furthermore, the phage solution eluted from MBEC4 cells were amplified by the method indicated below in "3-2-2. Phage amplification and purification" and used for the next panning round.

After eight rounds of in vitro panning, the phages were cloned.

3-2-1. Phage Titration

Titers of the phage solutions were measured as follows.

To 14-ml snap cap tubes, 250 µL of the overnight culture of BL21 or BLT5403 was added, and 2.5 ml of dissolved Top Agarose (6 µg/ml Agarose in LB broth) was added and mixed. This was immediately spread on LB plates to produce a BL21 round plate and a BLT5403 round plate. Using SM buffer, a series of dilutions of the phage solution whose titer is to be measured were prepared, and these solutions were blotted in 10 µL aliquots on the BL21 round plates and BLT5403 round plates, dried until the solutions were no longer flowing, and then cultured for 2 to 4 hours at 37° C. The titers of the phage solutions were calculated by counting the number of plaques formed. Phages that have a portion of the cDNA of rRNA (5'-CAC CAA GCG TTG GAT TGT TCA CCC ACT AAT AGG GAA CGT GAG CTG GGT TTA GAC CGT CGT GAG ACA GGT TAG TTT TAC CCT ACT GAT GAT GTG TTG TTG CCA TGG TAA TCC TGC TCA GTA CGA GAG GAA CCG CAG GTT CAG ACA TTT GGT GTA TGT GCT TGG CTG AGG AGC CAA TGG GGC GAA GCT ACC ATC TGT GGG ATT ATG ACT GAA CGC CTC TAA GTC AGA. ATC CCG CCC AG-3'/SEQ ID NO: 20) incorporated into the T7 rRNA: T7 Select 1-1kit (NEB, 70010-3), which was used as an internal standard in "3. In vivo panning" of the aforementioned Example 2, could not grow in BL21, and formed plaques only whenBLT5403 was used as the host.

3-2-2. Phage Amplification and Purification

An LB medium to which 1/100 volume of a BL21 overnight culture has been added was cultured at 37° C. for 2 to 3 hours with shaking in a conical flask with baffles, and then a phage solution to be amplified was added and this was further cultured for 1 to 3 hours with shaking (the amount of lysed *E. coli* debris and the decrease in turbidity were used as indicators). Subsequently, the culture was centrifuged at 10,000 rpm for 10 minutes at 4° C., and the supernatant was collected.

This supernatant was left to stand on ice overnight after adding ½ volume of 30% PEG/3 M NaCl, and the phages were precipitated. Next, this was centrifuged at 10,000 rpm at 4° C. for 45 minutes, the supernatant was removed by decantation and after further centrifugation at 10,000 rpm for 10 minutes at 4° C., phage precipitate was collected. The phage precipitate was completely dissolved in 2 ml of SM buffer, and this solution was centrifuged at 10,000 rpm for 5 minutes at 4° C. The supernatant was then collected, and following CsCl addition to the supernatant at 0.5 g/ml, density gradient centrifugation was carried out at 80,000 rpm for 18 hours at 15° C., and a band representing the purified phage was collected. The collected purified phage was dialyzed against SM buffer to remove CsCl, and stored at 4° C. after adding a few drops of chloroform.

4. Cloning

A series of dilutions of the phage eluate from the 8th round of in vitro panning was produced using the SM buffer, phage plaques were formed according to the method of "3-2-1. Phage titration", and then single plaques were picked and each placed in 1 ml of SM buffer. This procedure was repeated once more to clone the phage.

5. Sequencing

A portion of the phage clone was diluted 100-fold with MilliQ water, heated at 95° C. for 5 minutes, and then immediately cooled on ice to prepare a PCR template. 1 µL of this template was added, 5'-GCT CTG CGG TAG GTA CTG TT-3' (SEQ ID NO: 21) and 5'-CGG TGC CCC AAA-GAATCG GT-3' (SEQ ID NO: 22) were added as primers (1 µM each), and PCR was performed on a 30-µL scale as described below. Forty reaction cycles (94° C. for 1 minute, 60° C. for 1 minute, and 72° C. for 2 minutes) were performed. Subsequently, the PCR products were precipitated with ethanol, and the precipitates were dissolved in 10 µL of TE. Next, the PCR products were purified using CHROMA SPIN+TE30 Column (Clontech, K1321-2) to prepare the sequence template.

Sequence samples were prepared using the Thermo Sequence Cy5.5 Dye Terminator Kit (Amersham), and the sequences were determined on Gene Rapid SEQ 4×4.

The phage clones were purified as indicated above in "3-2-2. Phage amplification and purification", and used for in vivo evaluations.

6. Evaluation of Phage Clones 6-1. Phage Injection

Eight-week old male C57BL mice were used for in vivo panning. The T7 Select 415-c15c library (4×10$^6$ pfu/200 µL PBS) was sterilized and purified by 1 hour of UV irradiation, and administered to the left carotid artery of the mice under ether anesthesia for masking. Five minutes later, 200 µL of a phage mixture solution containing (4×10$^6$ pfu each) a purified T7 Select 415-c15c clone and T7 rRNAs as an internal standard was administered. One minute later, a tuberculin syringe (26G) coated with 15 mg/ml EDTA was used to draw blood from the hearts, and perfusion was carried out immediately with 400 ml of 0.2 g/ml EDTA-PBS. When perfusion was completed, the cardiac perfusate was collected. After perfusion, the brains were removed, and a portion of each was sampled for titration and tissue section preparation. The left brains were used for titration, and the right brains were used for section preparation.

6-2. Tissue Sample Preparation

The tissues for titration were weighed, and homogenized on ice after a double volume of the homogenization solution (20 mM HEPES/0.25 M sucrose/1 mM EDTA supplemented with 10 µg/ml aprotinin, 5 µg/ml leupeptin, and 1 mM PMSF immediately before use) was added. Next, a volume of 100 mM LiCl/PBS equivalent to the amount of the added homogenization solution was added and mixed.

The blood was centrifuged at 15,000 rpm for 10 minutes at 4° C. and collected as plasma, and the titer measured.

Phage titers of the homogenates, plasma, and perfusates of each of the tissues were determined by the method described above in "3-2-1. Phage titration".

Recombinant phages having an affinity to each of the organs were isolated from the tissue samples. Phages recovered from the brains were grown and again injected into mice at their tail vein, and an analysis similar to that described above was performed. As a result, several positive clones were isolated. Representative sequences are shown below.

Sequence 1: MLGDPN-CVKQAVQSSVKHPDLSC-KLAAALE (SEQ ID NO: 23)

Sequence 2: MLGDPN-CPRGLPVTTRLMEKSKC-KLAAALE (SEQ ID NO: 24)

Figure 6:
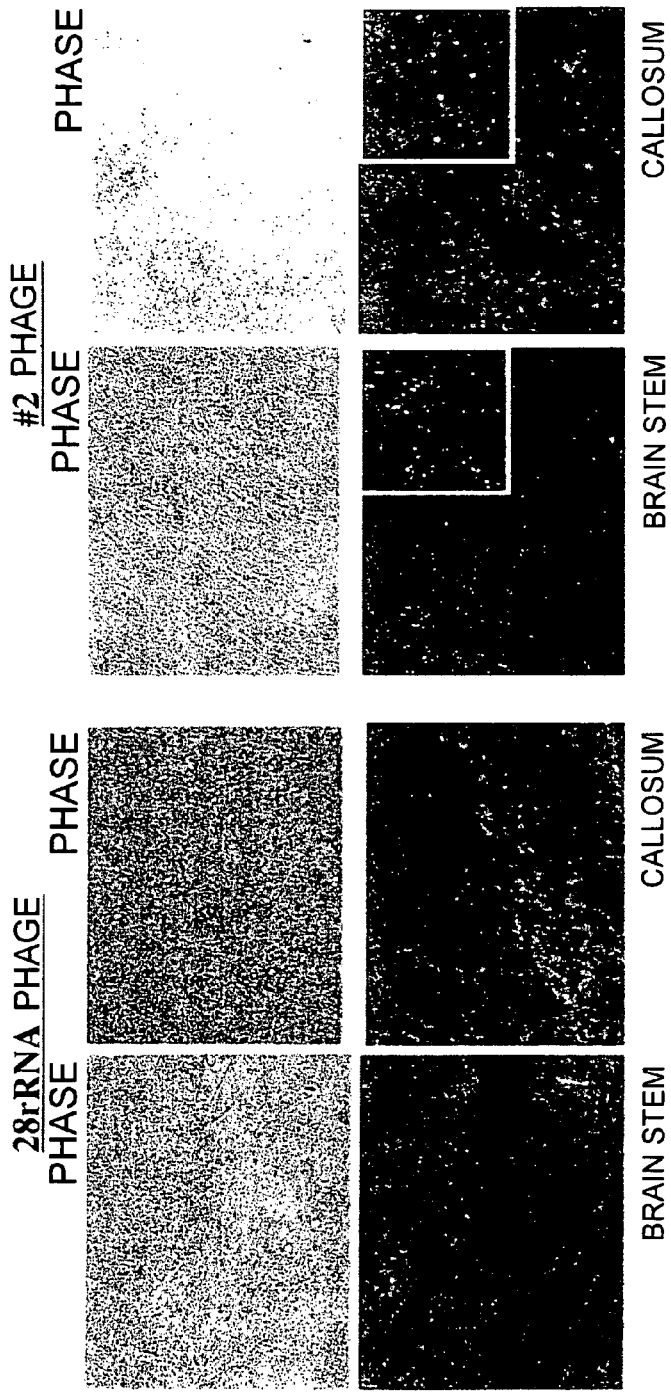
FIG. 6 is a set of photographs showing the brain-localizing activity of phages comprising the sequence of SEQ ID NO: 23 or 24.
Figure 7:
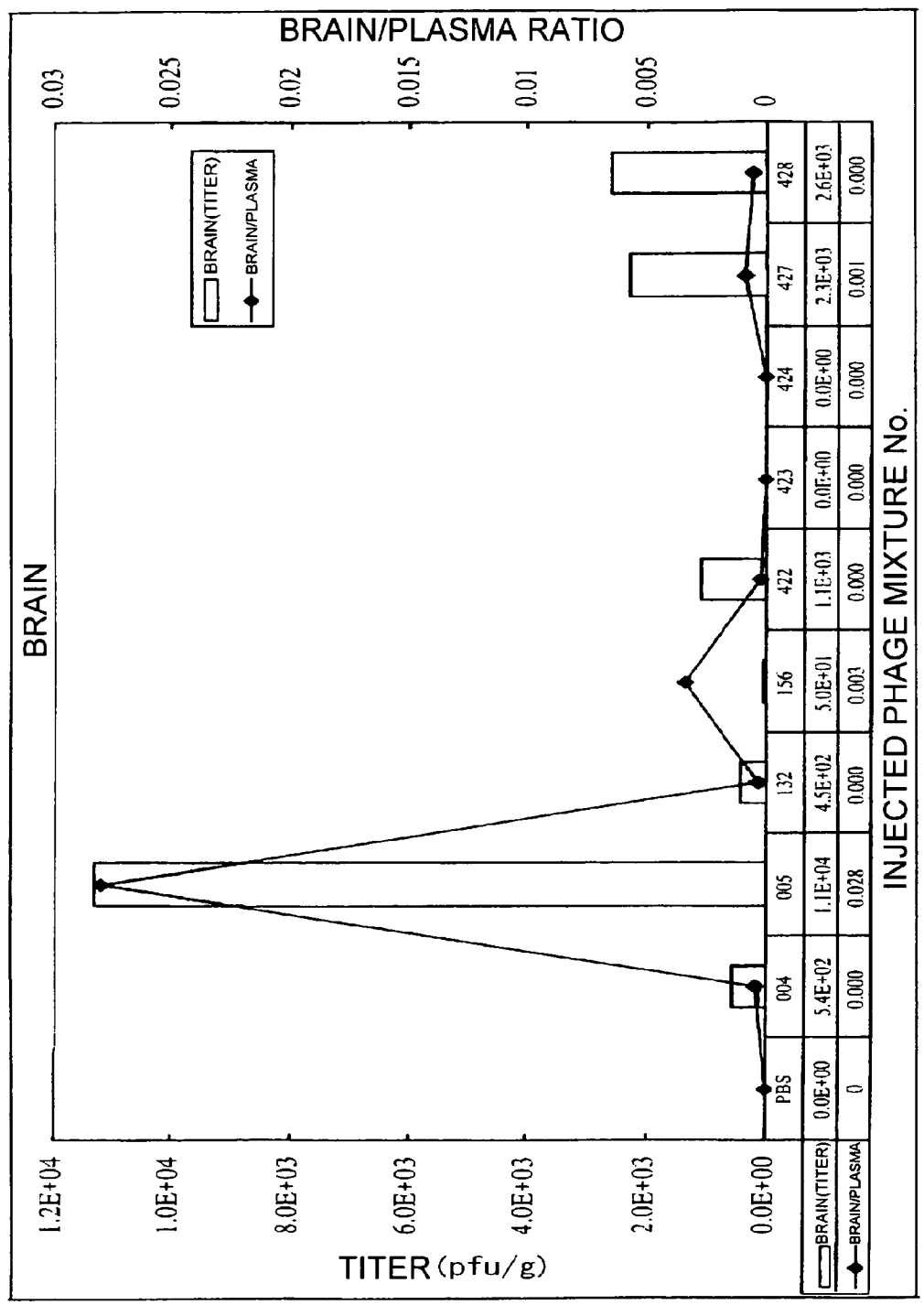
FIG. 7 is a graph showing the phage titer in brain and the brain/plasma ratio.

Phage clones comprising these sequences were injected into mice and were found to localize to the brain (FIGS. 6 and 7). Thus, the above-described method enabled isolation of candidate molecules that penetrate specifically into the brain.

Furthermore, by a similar method, molecules that can specifically target organs other than the brain may be isolated. In fact, as shown in FIG. 7, phages having affinity to organs other than the brain were isolated.

EXAMPLE 4

Brain-Localizing Peptide Conjugates

Figure 8:
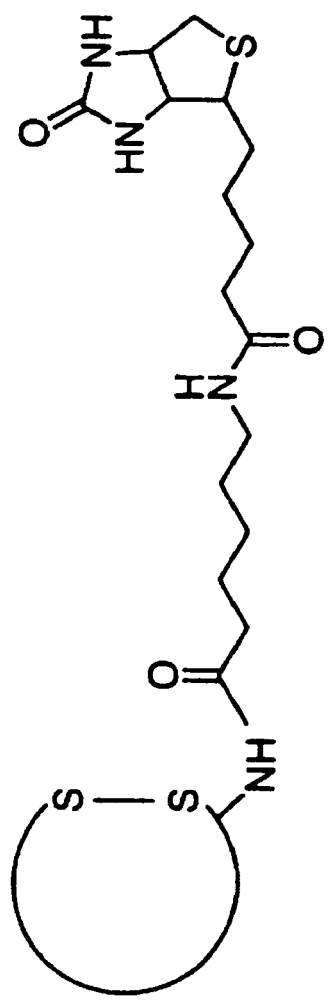
FIG. 8 shows a schematic structure of a brain localizing peptide conjugate of the present invention.

The present inventors produced brain-localizing peptide conjugates. The conjugates are molecules that can have a cyclic structure due to the formation of a disulfide bond between cysteine residues in a peptide molecule of the present invention, and may also have biotin attached to them. A more specific example is the structure shown in FIG. 8. The conjugates have affinity to avidin compounds.

The conjugates were bound to gold colloids and administered to mice, and the mice were subjected to experiments that evaluate the brain-localizing activity of the peptides of the present invention (observation of brain tissue sections under a transmission electron microscope). The protocol for producing transmission electron microscopy samples is shown in Table 2.

TABLE 2

| [Block preparation] | | |
|---|---|---|
| (i) prefixation: | 2.5% glutaraldehyde solution in 0.1 M PB at 4° C. | |
| (ii) washing: | 0.1 M PBS, cooled once or twice on ice | |
| (iii) postfixation: | 1% osmium tetroxide solution in 0.1 M PB, cooled on ice for approximately 1 hour | |
| (iv) dehydration: | ethanol series 70 → 80 → 90 → 95 → 100 → 100 → 100 (%), 10 minutes each | |
| (v) resin embedding: | Epok 812 resin polymerization at 35° C. for 12 hours; 45° C., 12 hours; and 60° C., 20 hours | |

[Section Preparation]
(i) trimming
(ii) preparation of thick sections (2 to 3 μm thick) using a glass knife
(iii) preparation of ultra-thin sections (50 to 100 nm thick) using a diamond knife
(iv) electron staining: 2% uranium acetate and then 1% lead citrate (3 minutes each)
(v) transmission electron microscope observation (acceleration voltage of 80 kV)

Figure 9:
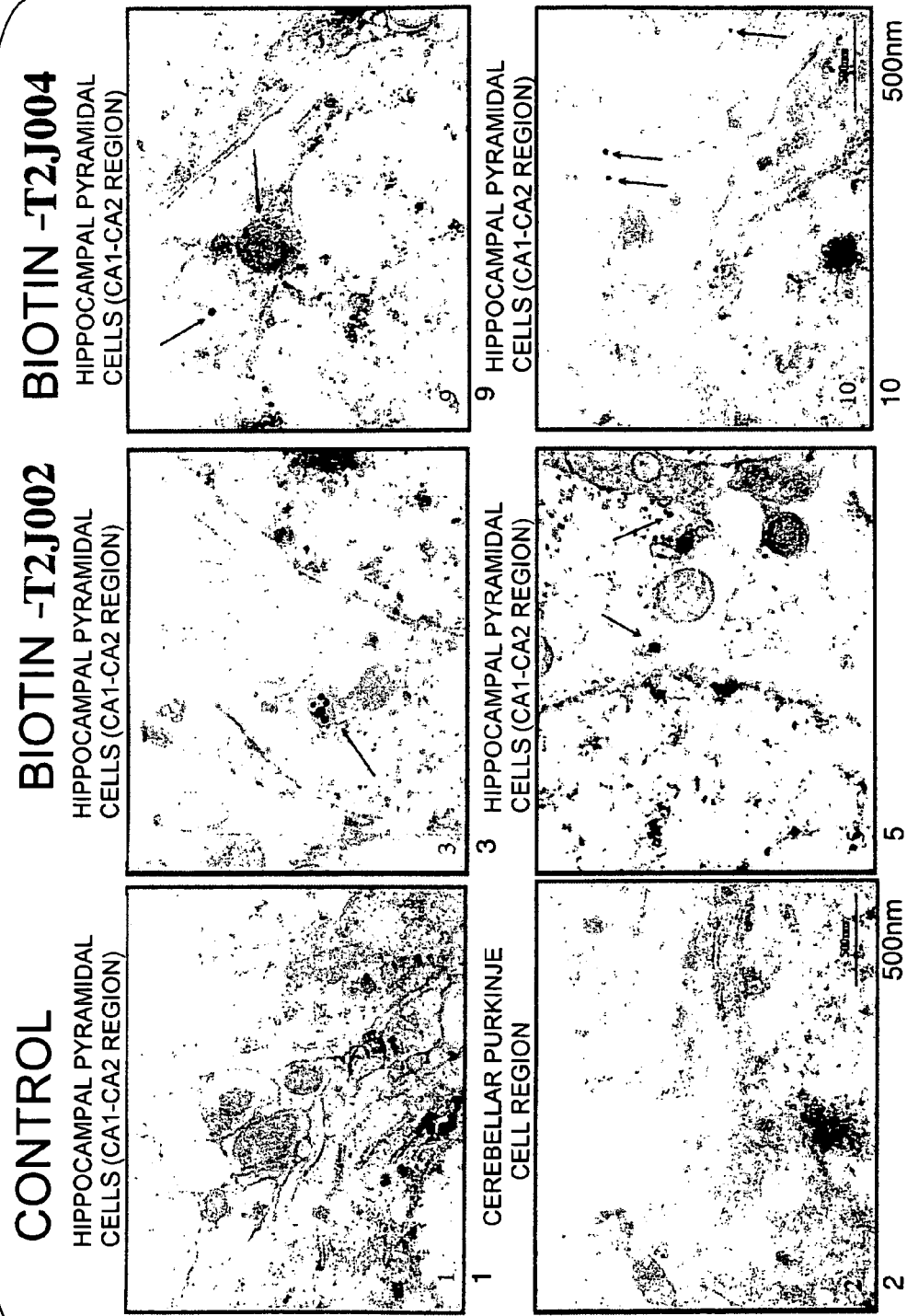
FIG. 9 is a set of electron micrographs showing the presence of conjugates with a peptide of the present invention and colloidal gold in mouse brains.

In the present experiment, T2J002 (SEQ ID NO: 2) and T2J004 (SEQ ID NO: 4) were used as peptides of the present invention. The electron micrographs of mouse brain tissues (cells) are shown in FIGS. 9 and 10. The arrows show positions of the gold particle-bound peptide molecules of the present invention. The results show that the peptide conjugates of the present invention successfully transport the gold colloids into the cerebral parenchyma. More specifically, the peptides of the present invention were confirmed to have brain-localizing activity.

EXAMPLE 5

T2J004Y-Biotin Permeation Experiment

The following reagents were used: streptavidin, FITC conjugate (Vector; 1.0 mg/ml), T2J004-Biotin, plus DMEM (SIGMA) 10% FBS (GIBCO lot. 1077859) for MBEC4 experiments and DMEM+10% FBS (GIBCO lot. 1077859: inactivated at 65° C. for 30 minutes) for END-D experiments. The above-mentioned "T2J004Y-Biotin" comprises the polypeptide shown in SEQ ID NO: 4.

First, MBEC4 ($1.26 \times 10^4$/insert), and END-D ($2 \times 10^4$/insert) were seeded in cell culture inserts (FALCON [35] 3096; 3.0 μm pore size) and cultured at 37° C. under 5% $CO_2$ for 4 days.

Streptavidin, FITC conjugate (25 μL/insert) and T2J004Y-Biotin (1.6 nmol/insert) were mixed and incubated for 30 minutes at room temperature. Subsequently, the volume was adjusted to 250 μL with each culture medium to replace the medium in the insert, and 750 μL of culture medium was added to each of these wells (FALCON 24-well plate for cell culture insert). 100 μL were sampled from each well 3, 6, and 24 hours later, and fluorescence intensity was measured using Fluoroskan Ascent (Thermo Labsystems). The present experiment is outlined in FIG. 11.

As a result, the permeability of FITC-conjugated T2J004Y-Biotin was approximately eight-fold greater and approximately four-fold greater in MBEC4 and END-D, respectively, when compared to that of the FITC alone. Furthermore, peptide permeability into MBEC4 was more than twice of that in END-D, and the amount of permeation increased with time.

EXAMPLE 6

Relationship Between the Amount of T2J004Y-Biotin Added and Permeation Amount in MBEC4

Avidin and biotin bind at a ratio of 1:4. The proportion of T2J004Y-Biotin to be reacted with streptavidin-FITC was changed, and the amount of permeation in MBEC4 was examined.

The following reagents were used: streptavidin, FITC conjugate (Vector; 1.0 mg/ml), T2J004Y-Biotin, DMEM+10% FBS.

First, MBEC4 ($1.26 \times 10^4$/insert) was seeded and cultured at 37° C. under 5% $CO_2$ for 4 days. Streptavidin-FITC conjugates (25 μL/insert) mixed with 1.6 nmol/insert, 0.4 nmol/insert, and 0.2 nmol/insert of T2J004Y-Biotin were added to the cells and incubated at room temperature for 30 minutes. The volumes of the mixed solutions were adjusted to 250 μL with the culture medium to replace the medium in the insert. 750 μL of the culture medium was added to each well, and fluorescence intensity was measured 3 hours and 6 hours later using Fluoroskan Acsent.

The amount of peptide permeation correlated with the amount of peptide added. However, compared to the addition of 0.4 nmol/insert peptide, the addition of 1.6 nmol/insert peptide—an amount four times greater—resulted in only about a two-fold increase in the amount of peptide permeation. Therefore, 1.6 nmol/insert of the peptide seems to be sufficient for permeation in 6 hours through an MBEC4 sheet having an effective insert culture surface area of 0.3 $cm^2$ (FIG. 12).

EXAMPLE 7

Inhibition of T2J004Y-Biotin Permeation by Peptides

Whether T2J004Y-Biotin-FITC permeation was inhibited by pretreatment with non-biotinylated peptides was examined.

The following reagents were used: streptavidin, FITC conjugate (Vector; 1.0 mg/ml), T2J004Y-Biotin, DMEM+10% FBS for MBEC4 experiment, CT2J004Y, and LT2J004Y. ("CT2J004Y" refers to a molecule with a cyclic structure, and "LT2J004Y" refers to a molecule with a linear structure. The cyclic structure is formed by a disulfide bond between cysteine residues in the molecule.)

First, each of the peptides (10 nmol/insert) that had not been biotinylated was mixed with the culture medium (200 μL/insert) to replace the insert culture medium used for 4 days of culturing under the aforementioned conditions. Thirty minutes later, the peptide-FITC mixture that had been mixed in the same manner described above was adjusted to 50 μL with the culture medium, and added to the insert. Six hours later, the contents of the 24 wells were stirred well, and fluorescence intensity was measured using Fluoroskan Ascent.

As a result, both CT2J004Y and LT2J004Y individually suppressed the permeation of T2J004Y-Biotin-FITC by approximately 25% (FIG. 13).

EXAMPLE 8

Inhibition of Microglia Permeation by Pretreating Phages

The following reagents were used: PKH57 Green Fluorescent Cell Linker Kit for general cell membrane labeling (SIGMA), and DMEM+10% FBS.

First, MBEC4 cells ($1.26 \times 10^4$/insert) were seeded in inserts and cultured at 37° C. under 5% $CO_2$ for 4 days, then 5 μL of the control and 5 μL of phages presenting brain-localizing peptides ($10^{13}$ pfu/ml) were added thereto, followed by 1 hour of pretreatment. After microglial cell membrane was stained with PKH26, 2×1 cells/insert were placed in DMEM+10% FBS to prepare 250-μL samples and added. 750 μL of culture medium was added to the well, and 24 hours later, the numbers of microglias at the bottom of the well and in the culture were counted. FIG. 14 shows an outline of the present experiment.

As a result, compared to the control phage, the phages presenting brain-localizing peptides seemed to somewhat inhibit permeation of the microglias through MBEC4. A clear difference was not observed probably because the number of phages and microglia serving as ligands was small compared to the number of receptors on MBEC4.

EXAMPLE 9

Comparison of the Permeability of T2J004Y-Biotin and Other Peptides

The following reagents were used: streptavidin, FITC conjugate (Vector; 1.0 mg/ml), T2J004Y-Biotin, T2J002Y-Biotin, T2J003Y-Biotin, DMEM+10% FBS for MBEC4.

First, MBEC4 cells ($1.26\times10^4$/insert) were seeded in inserts, and cultured at 37° C. under 5% $CO_2$ for 4 days. Streptavidin, FITC conjugate (25 µL/insert), and 1.6 nmol/insert of each T2J004Y-Biotin, T2J002Y-Biotin, and T2J003Y-Biotin were mixed individually, and incubated at room temperature for 30 minutes. Subsequently, the mixtures were adjusted to 250 µL with each culture medium to replace the culture medium in the inserts, and then 750 µL of the culture medium was added to each well (FALCON 24-well plate for cell culture inserts). 100 µL was sampled from the wells 3, 6, and 24 hours later, and fluorescence intensity was measured using Fluoroskan Ascent.

The results of the permeation ratios of T2J002Y-Biotin and T2J003Y-Biotin were indicated by taking the MBEC4 permeability of T2J004Y-Biotin to be 100. The permeability of T2J002Y-Biotin was only 20 to 40% of that of T2J004Y-Biotin, but the permeability of T2J003Y-Biotin was approximately 1.4-fold higher (FIG. 15).

EXAMPLE 10

Brain-Localizing Activity of Phages Expressing the Peptides of the Present Invention Phages that express the peptides of the present invention and a control phage were administered intravascularly, and brain-localizing activities were examined.

As a result, phage particles expressing the peptides of the present invention were detected in the brain (FIG. 16).

EXAMPLE 11

Transcytosis Activity of Microglial Cells

Transcytosis activity of microglias was observed in the blood-brain barrier model using MBEC4.

Transcytosis was detected 4 hours after microglia addition (FIG. 17).

Furthermore, the transcytosis activity at the time of microglias passing through the blood-brain barrier model was observed using an electron microscope.

As a result, images of microglial protrusions penetrating into the MBEC4 cells that formed the blood-brain barrier were clearly observed (FIGS. 21 and 22).

Furthermore, as a control experiment, a similar experiment was performed using macrophages. The macrophages only adhered loosely to the MBEC4 cells that form the blood-brain barrier, and did not permeate into the cell layer (FIGS. 23 and 24).

INDUSTRIAL APPLICABILITY

The present inventors are the first to reveal amino acid motif sequences involved in brain-localizing activity, and discovered that polypeptides comprising the motif sequences have brain-localizing activity. The polypeptides of the present invention specifically bind to cerebrovascular endothelial cells, and induce a transcellular pathway to enable transport of substances into the cerebral parenchyma.

---

The invention claimed is:

1. An isolated polypeptide comprising:
(a) a polypeptide comprising any one of the amino acid sequences set forth in SEQ ID NOs: 1 and 3 to 12; or
(b) a polypeptide comprising a peptide region cyclized by a disulfide bond formed between cysteine residues on both ends of the polypeptide of (a).

2. The polypeptide of claim 1, wherein the length of the polypeptide is 9 amino acids or less.

3. A pharmaceutical agent for conferring brain-localizing activity to an arbitrary molecule, wherein the agent comprises the polypeptide of claim 1.

4. The pharmaceutical agent of claim 3, wherein the arbitrary molecule is an arbitrary polypeptide.

5. A molecule having brain-localizing activity, wherein the molecule comprises the polypeptide of claim 1.

6. The molecule of claim 5, wherein the molecule is a phage particle or a coat protein of a phage particle.

7. The molecule of claim 5, wherein the molecule is a fusion protein formed with an isolated polypeptide of any one of (a) to (b) described below:
(a) a polypeptide comprising any one of the amino acid sequences set forth in SEQ ID NOs: 1 and 3 to 12; and
(b) a polypeptide comprising a peptide region cyclized by a disulfide bond formed between cysteine residues on both ends of the polypeptide of (a).

8. A carrier for delivery to the brain, wherein the carrier comprises the polypeptide of claim 1.

9. A carrier for delivery to the brain, wherein the carrier comprises a structure in which the polypeptide of claim 1 is bound to a micelle, liposome, or microcapsule.

10. A therapeutic agent for brain disease, wherein the agent comprises a structure in which a drug is supported by the carrier of claim 8.

11. A method for producing a molecule having brain-localizing activity, wherein the method comprises binding to an arbitrary molecule a polypeptide comprising any one of the amino acid sequences set forth in SEQ ID NOs: 1 and 3 to 12.

12. A method for translocating an arbitrary molecule into the brain of an animal, wherein the method comprises the steps of:
(a) producing a molecule having brain-localizing activity, wherein the molecule comprises a structure in which an arbitrary molecule is bound to a polypeptide comprising any one of the amino acid sequences set forth in SEQ ID NOs: 1 and 3 to 12; and
(b) administering the molecule into the body of the animal.

13. A method of screening for a molecule having binding activity to a polypeptide comprising any one of the amino acid sequences set forth in SEQ ID NOs: 1 and 3 to 12, wherein the method comprises the steps of:
(a) contacting with a test molecule a polypeptide comprising any one of the amino acid sequences set forth in SEQ ID NOs: 1 and 3 to 12;
(b) detecting binding activity between the polypeptide and the test molecule; and
(c) selecting a molecule that binds to the polypeptide.

14. A therapeutic agent for brain disease, wherein the agent comprises a structure in which a drug is supported by the carrier of claim 9.

* * * * *